US011366063B2

(12) United States Patent
Aronov et al.

(10) Patent No.: US 11,366,063 B2
(45) Date of Patent: *Jun. 21, 2022

(54) SENSOR PLANT AND METHOD FOR IDENTIFYING STRESSORS IN CROPS BASED ON CHARACTERISTICS OF SENSOR PLANTS

(71) Applicant: InnerPlant, Inc., San Francisco, CA (US)

(72) Inventors: Shely Aronov, San Francisco, CA (US); Roderick Kumimoto, San Francisco, CA (US); Nicholas Koshnick, San Francisco, CA (US); Ari Kornfeld, San Francisco, CA (US)

(73) Assignee: InnerPlant, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/479,965

(22) Filed: Sep. 20, 2021

(65) Prior Publication Data
US 2022/0003677 A1 Jan. 6, 2022

Related U.S. Application Data

(63) Continuation of application No. 16/721,830, filed on Dec. 19, 2019.
(Continued)

(51) Int. Cl.
*G01N 21/64* (2006.01)
*A01G 25/16* (2006.01)
(Continued)

(52) U.S. Cl.
CPC ......... *G01N 21/6486* (2013.01); *A01G 25/16* (2013.01); *B64D 47/08* (2013.01); *B64G 1/1021* (2013.01); *B64G 2001/1028* (2013.01)

(58) Field of Classification Search
CPC .... G01N 21/6486; A01G 25/16; B64D 47/08; B64G 1/1021; B64G 2001/1028
See application file for complete search history.

(56) References Cited

U.S. PATENT DOCUMENTS 7,715,013 B2 * 5/2010 Glaser ............... G01N 21/4738
356/448
9,945,828 B1 4/2018 Poling et al.
(Continued)

FOREIGN PATENT DOCUMENTS

WO 2020068694 A1 4/2020

OTHER PUBLICATIONS

Liew et al. "Signature Optical Cues: Emerging Technologies for Monitoring Plant Health" Sensors 2008, 8, 3205-3239; DOI: 10.3390/s8053205 (Year: 2008).*
(Continued)

*Primary Examiner* — Richard A Hansell, Jr.
(74) *Attorney, Agent, or Firm* — Run8 Patent Group, LLC; Peter Miller; Leah Raddatz

(57) ABSTRACT

One variation of a method for identifying stressors in crops based on fluorescence of sensor plants includes: accessing a set of spectral images of a sensor plant sown in a crop, the sensor plant of a sensor plant type including a set of promoters and a set of reporters configured to signal a set of stressors present at the sensor plant, the set of promoters and set of reporters forming a set of promoter-reporter pairs; accessing a reporter model linking characteristics extracted from the set of spectral images of the sensor plant to the set of stressors based on signals generated by the set of promoter-reporter pairs in the sensor plant type; and identifying a first stressor, in the set of stressors, present at the sensor plant based on the reporter model and characteristics extracted from the set of spectral images.

18 Claims, 10 Drawing Sheets

Related U.S. Application Data

(60) Provisional application No. 62/894,676, filed on Aug. 30, 2019, provisional application No. 62/864,401, filed on Jun. 20, 2019, provisional application No. 62/782,130, filed on Dec. 19, 2018.

(51) Int. Cl.
  *B64G 1/10* (2006.01)
  *B64D 47/08* (2006.01)

(56) References Cited

U.S. PATENT DOCUMENTS

| | | |
|---|---|---|
| 10,354,189 B2* | 7/2019 | Volkov .................... G06N 5/04 |
| 2003/0138812 A1* | 7/2003 | Downs ................... G01N 33/50 |
| | | 435/5 |
| 2005/0072935 A1* | 4/2005 | Lussier .............. G01N 21/6486 |
| | | 250/458.1 |
| 2008/0047039 A1 | 2/2008 | Hinchey |
| 2010/0111369 A1 | 5/2010 | Lussier |
| 2012/0245473 A1* | 9/2012 | Mycek ................. G01N 21/474 |
| | | 600/479 |
| 2013/0266221 A1* | 10/2013 | Kaneko ..................... G06T 5/00 |
| | | 382/168 |
| 2014/0007293 A1 | 1/2014 | Stewart et al. |
| 2014/0059722 A1 | 2/2014 | Krichevsky |
| 2015/0027040 A1 | 1/2015 | Redden |
| 2016/0069743 A1 | 3/2016 | McQuilkin et al. |
| 2017/0030877 A1* | 2/2017 | Miresmailli ........... G06N 20/00 |
| 2017/0121733 A1 | 5/2017 | Repetti et al. |
| 2017/0131254 A1 | 5/2017 | Shriver et al. |
| 2018/0259496 A1 | 9/2018 | McPeek |
| 2019/0003972 A1* | 1/2019 | Gu ..................... G01N 21/6486 |
| 2019/0108413 A1 | 4/2019 | Chen et al. |
| 2020/0302338 A1* | 9/2020 | Carroll ................. A01G 27/003 |

OTHER PUBLICATIONS

Priego et al. "Detection of Water Stress in Orchard Trees With a High-Resolution Spectrometer Through Chlorophyll Fluorescence In-Filling of the O2—A Band", IEEE Transactions on Geoscience and Remote Sensing, vol. 43, No. 12, Dec. 2005 (Year: 2005).*
Band et al. "Root gravitropism is regulated by a transient lateral auxin gradient controlled by a tipping-point mechanism." Proceedings of the National Academy of Sciences 109.12 (2012): pp. 4668-4673.
Fethe, "The Performance of Bacterial Phytosensing Transgenic Tobacco Under Field Conditions" (2013), Master's Thesis, University of Tennessee, 81 pages.
International Search Report and Written Opinion for International Patent Application No. PCT/US2019/67674, dated Jun. 10, 2020, 11 pages.
Notification of the International Application Number and of the International Filing Date for International Patent Application No. PCT/US2019/067674, dated Jan. 17, 2020, 1 page.
International Search Report dated Jun. 10, 2020 received in PCT/US19/67674—All references cited in this report have been cited in U.S. Appl. No. 16/721,830 in an Information Disclosure Statement filed Jul. 10, 2020.
International Search Report dated Sep. 4, 2020 received in PCT/US20/39001.
Chinese Office action received in CN App. No. 20198009562.4 dated Dec. 21, 2021.
Liew et al., Signature Optical Cues: Emerging Technologies for Monitoring Plant Health, Sensors 2008, 8, 3205-3239.

* cited by examiner

SENSOR PLANT AND METHOD FOR IDENTIFYING STRESSORS IN CROPS BASED ON CHARACTERISTICS OF SENSOR PLANTS

CROSS-REFERENCE TO RELATED APPLICATIONS

This Application is a continuation of U.S. patent application Ser. No. 16/721,830, filed on 19 Dec. 2019, which claims the benefit of U.S. Provisional Application No. 62/894,676, filed on 30 Aug. 2019, U.S. Provisional Application No. 62/864,401, filed on 20 Jun. 2019, and U.S. Provisional Application No. 62/782,130, filed on 19 Dec. 2018, each of which are incorporated in its entirety by this reference.

TECHNICAL FIELD

This invention relates generally to the field of agriculture and more specifically to a new and useful sensor plant and method for identifying stressors in crops based on characteristics of sensor plants in the field of agriculture.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Sensor Plant

Figure 1:
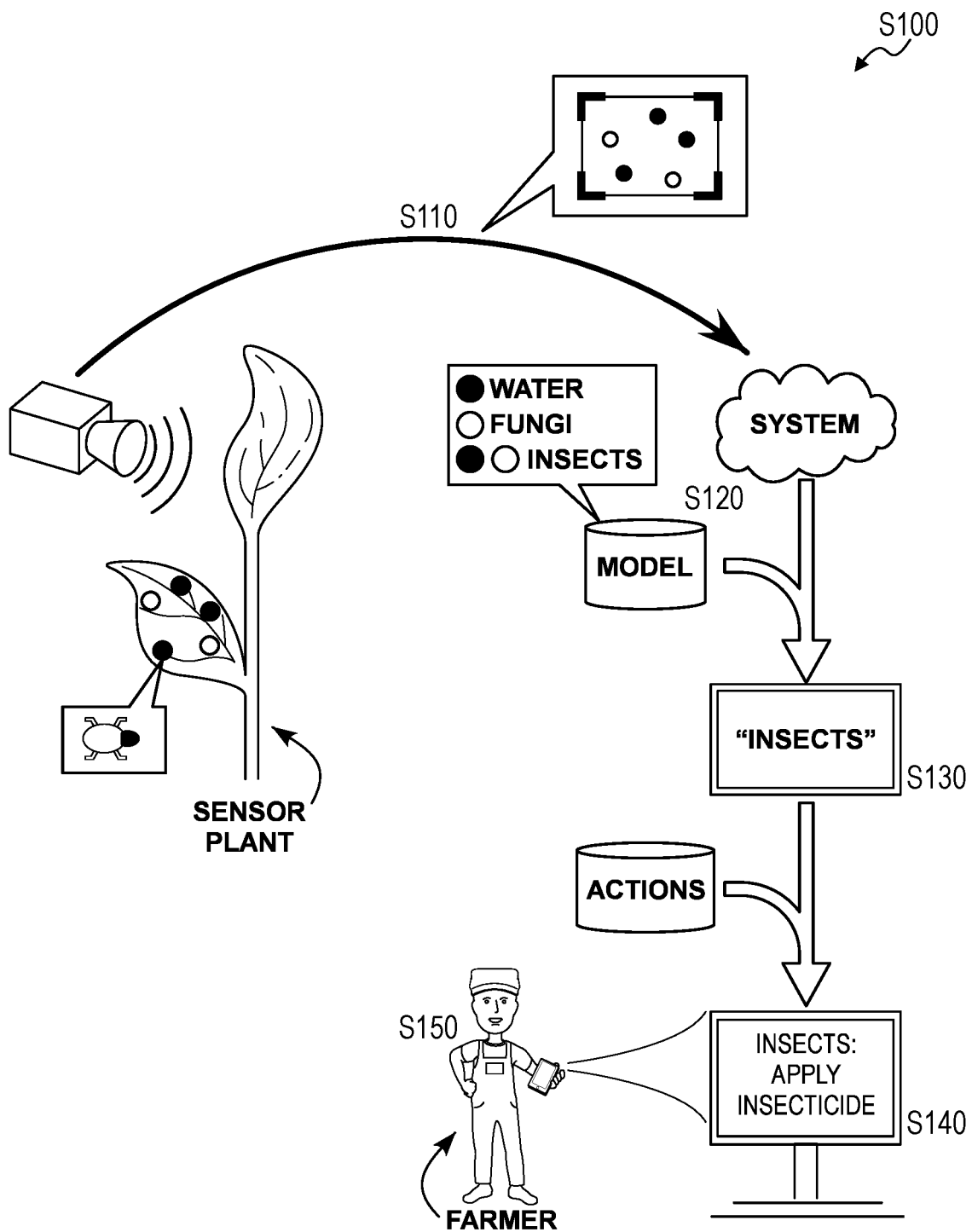
FIG. 1 is a flowchart representation of a first method.

As shown in FIG. 1, a sensor plant includes a first promoter-reporter pair including: a first promoter that activates in the presence of a first stressor at the sensor plant; a first reporter coupled to the first promoter and configured to exhibit a first signal in the electromagnetic spectrum in response to activation of the first promoter by the first stressor. The sensor plant includes a second promoter-reporter pair including: a second promoter that activates in the presence of a second stressor at the sensor plant; a second reporter coupled to the second promoter and configured to exhibit a second signal in the electromagnetic spectrum in response to activation of the first promoter by the second stressor, the second signal different from the first signal. The sensor plant further includes a third promoter that activates in the presence of a third stressor at the sensor plant; and the first reporter and the second reporter are coupled to the third promoter and are configured to exhibit a third signal in the electromagnetic spectrum in response to activation of the third promoter by the third stressor, the third signal different from the first signal and the second signal.

One variation of the sensor plant includes a first promoter-reporter pair including: a first promoter configured to activate in the presence of a first stressor within a first magnitude range at the sensor plant; and a first reporter coupled to the first promoter and configured to exhibit a first signal in the electromagnetic spectrum in response to activation of the first promoter by the first stressor. In this variation, the sensor plant also includes a second promoter-reporter pair including: a second promoter configured to activate in the presence of the first stressor within a second magnitude greater than the first magnitude range at the sensor plant; and a second reporter coupled to the second promoter and configured to exhibit a second signal in the electromagnetic spectrum in response to activation of the second promoter by the second stressor.

Another variation of the sensor plant includes: a first promoter that activates at a first time over a first duration in response to a first stressor presence in the sensor plant; a second promoter that activates at a second time for a second duration in response to the first stressor presence in the sensor plant, the second time succeeding the first and preceding the termination of the first duration; and a reporter coupled to the first and second promoter that, in response to activation of the first promoter, exhibits a first signal over the first duration for detection of the first stressor; and, in response to activation of the second promoter, exhibits a second signal over the second duration for detection of the first stressor.

1.1 Method

Figure 2:
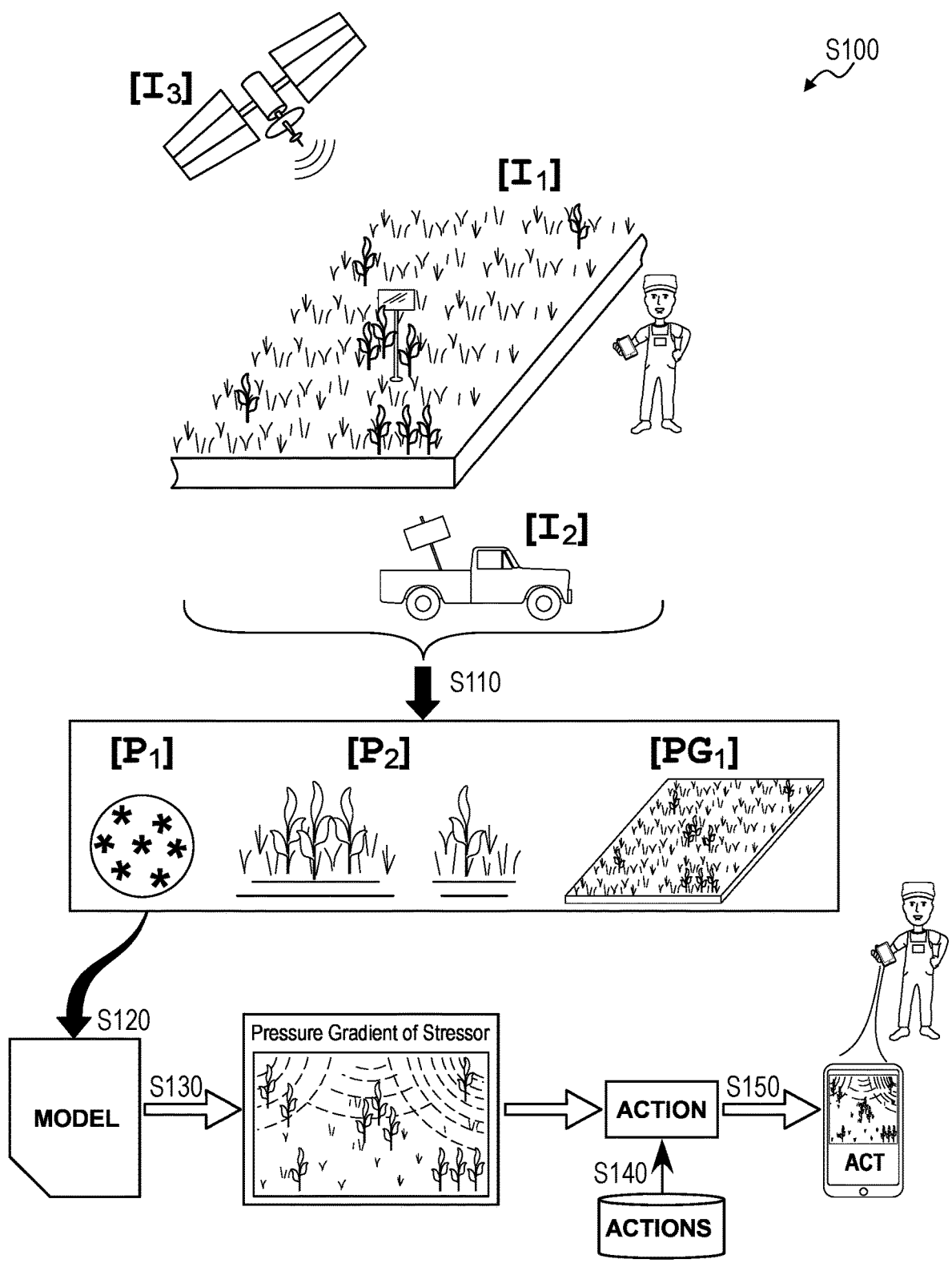
FIG. 2 is a flowchart representation of the first method.

As shown in FIGS. 1 and 2, a first method S100 for identifying stressors in crops based on characteristics of sensor plants includes: accessing an image of a sensor plant sown in a crop in Block S110, the sensor plant of a sensor plant type including a set of promoters and a set of reporters configured to signal a set of stressors present at the sensor plant, the set of promoters and set of reporters forming a set of promoter-reporter pairs; accessing a reporter model linking features extracted from images of the sensor plant type to the set of stressors based on signals generated by the set of promoter-reporter pairs in the sensor plant type in Block S120; identifying a first stressor, in the set of stressors, present at the sensor plant based on the reporter model and features extracted from the image in Block S130; isolating a first action, in a set of actions defined for the sensor plant type, linked to the first stressor in Block S140; and, in response to identifying the first stressor, prompting a farmer to perform the first action at the crop to mitigate the first stressor in Block S150.

1.2 Applications

Generally, a sensor plant includes a promoter-reporter pair configured to detect stressors present in the sensor plant and to produce a detectable signal (e.g., in the electromagnetic spectrum) to indicate presence of these stressors in the sensor plant or in a region of a crop where the sensor plant is located more generally. More specifically, a sensor plant can be genetically modified to include: a promoter gene sequence (hereinafter a "promoter") configured to activate in the presence of (e.g., "linked to") a particular stressor; and a reporter gene sequence (hereinafter a "reporter") paired to the promoter and configured to exhibit (or "express") a signal when the promoter is active.

A computer system (e.g., a remote server, a local device, a computer network) can then execute Blocks of the method to detect this signal in an image of this sensor plant and to interpret this signal as presence (and/or duration, magnitude) of this particular stressor. In particular, the computer system can: access an image of the sensor plant (e.g., the sensor plant specifically, a cluster of plants including the sensor plant, a whole crop field); detect the sensor plant in a region of the image; extract intensity of a particular signal (e.g., an electromagnetic signal in the visible light or infrared spectrum)—generated by a promoter-reporter pair for this sensor plant type in the presence of the particular stressor—from this region of the image depicting the sensor plant; and then predict presence of the particular stressor at the sensor plant if this intensity of the particular signal exceeds a threshold intensity. The computer system can additionally or alternatively: predict a duration of time that the particular plant pressure was present at the sensor plant; predict a magnitude of the particular plant pressure at the sensor plant based on this intensity of the particular signal; and/or isolate a particular course of action to address presence of the particular stressor at the sensor plant, such as based on a link between the particular signal and the particular course of action defined by the reporter model. Accordingly, the computer system can alert a farmer or other entity affiliated with the sensor plant or crop of presence, duration, and/or magnitude of the particular stressor in the sensor plant and/or prompt the farmer to perform the particular course of action at the sensor plant (and surrounding plants, field, or crop) to eradicate or mitigate the particular stressor.

In one implementation, an imaging system (e.g., a multispectral or hyperspectral imaging system) can capture digital images (e.g., spectral images) of a plant canopy (e.g., sensor plants and surrounding plants). For example, the imaging system can include: an optomechanical fore optic that enables measurement of fluorescent and non-fluorescent targets; and a digital spectrometer or digital camera that records images through the optomechanical fore optic. The computer system can thus access images recorded by the imaging system and process these images according to the method S100 to detect reporter signals and interpret pressures present in these plants.

In one variation, promoter-reporter pairs are incorporated into GMO plant genes within a GMO stack already present in GMO seeds, which may then be planted to produce an entire crop of sensor plants (e.g., non-sterile GMO sensor plants). These sensor plant seeds can be configured to generate several distinct signals that represent an array of stresses, as described below. For example, sensor plants including different promoter-reporter pairs can be distributed evenly throughout a crop. Alternatively, sensor plants can be planted in clusters within the field wherein all plants within each cluster contain the same promoter-reporter pair(s) configured to produce a particular signal responsive to a particular biotic or abiotic stressor (or for a particular set or class of biotic and/or abiotic stressors). For example, sensing plant seeds containing the same promoter-reporter pairs can be planted along the full length of one crop row in a field with (non-sterile) sensing plant seeds in the two adjacent crops rows containing different promoter-reporter pairs configured to produce different (or the same) signals responsive to different biotic or abiotic stressors. (In this example, this pattern of rows containing seeds with different promoter-reporter pairs can be repeated along the full length of the field.)

By thus clustering sensor plants in one-dimensional or two-dimensional groups of sensor plants including the same promoter-reporter pairs and therefore configured to produce signals responsive to the same stressors, the crop as a whole can produce high-amplitude signals—characterized by high signal-to-noise ratios—for multiple different biotic and/or abiotic stressors in discrete rows or regions of the field. The computer system can thus execute Blocks of the method S100 to interpolate or extrapolate stressors—indicated by these rows or clusters of sensor plants configured to produce signals responsive to these stressors—across the entire field in order to predict stressor pressures across the entire crop. Therefore, in this variation, because each plant in the field exhibits sensing capabilities, the computer system can monitor the entire crop directly via a fixed or mobile imaging system and can generate a pressure map of biotic and/or abiotic stressors for the crop as a whole based on signals produced by these sensor plants during over time (e.g., once per day) and detected in images of the crop. By repeating this process to develop new pressure maps for the field over time, the computer system can monitor stressors across the field over time and serve data and/or recommendations for proactive mitigation of these stressors to a farmer, agronomist, field operator, automated system, inputs supplier, or other entity affiliated with the field. The computer system can also implement this process to update the pressure map for the field following a stressor treatment at the field, thereby enabling a field operator to directly assess efficacy of this stressor treatment and to make more informed treatment decisions for the field in the future.

1.3 Promoter-Reporter Pair

A sensor plant can be genetically modified to include promoter and reporter pairs that indicate presence of stressors in the sensor plant. A promoter includes genetic regulatory elements that drive expression of mRNA at a specific time and place that is subsequently translated into a functional protein. Promoter activity is representative of native biological processes that occur when a particular stressor is present in the sensor plant. To detect presence of these stressors, a reporter that expresses a certain signal can be coupled to the promoter of choice. More specifically, the reporter can initiate a metabolic change in the sensor plant such that a detectable signal is produced (e.g., a pigmentation change in the sensor plant). Therefore, when the sensor plant's cells express the promoter associated with a particular stressor, the reporter tagged to the promoter is also expressed and produces a detectable signal. For example, the sensing plant can be genetically modified to fluoresce (i.e., absorb photons at one frequency and emit photons at a different frequency) in the presence of (and proportional to) a disease or stressor pressure. In this example, the sensing plant can be modified to fluoresce in the presence of one or more disease or stressor pressures, such as: fungi, bacteria, nematodes, parasites, viruses, insects, heat, water stress, nutrient stress, phytoplasmal disease, etc.

In one example, the sensor plant is genetically modified to include a promoter with activity representative of a native biological process that occurs in the presence of an insect pressure in the sensor plant. In this example, the promoter is paired to a red fluorescence protein reporter such that the resulting promoter-reporter pair is configured to exhibit red fluorescence in presence of the insect pressure in the sensor plant.

In one variation, the sensor plant can be genetically modified to include a particular promoter-reporter pair. For example, at a first time, the sensor plant can be genetically modified via genetic engineering techniques to associate bioluminescence of the sensor plant (initiated by a reporter) to a promoter linked to a particular metabolic process indicative of water stress in the sensor plant. At a later time, in response to a water level in the sensor plant cells falling below a minimum water concentration, the sensor plant can: initiate the particular metabolic process, and therefore express the promoter; express the reporter and initiate a metabolic process linked to plant bioluminescence; and signal—via bioluminescence of the sensor plant—a water concentration below the minimum water concentration.

Therefore, the sensor plant can include a promoter-reporter pair configured to signal presence of particular biotic and/or abiotic pressures experienced by the sensor plant, such as pest, disease, water, heat, soil health, and/or nutrient stresses or deficiencies. For example, the sensor plant can be genetically modified to include a promoter with activity linked to presence of one stressor at the plant, such as a fungal, pest, heat, water, disease, or nutrient stress. The sensor plant can also be genetically modified to include a reporter paired with the promoter and configured to produce a detectable signal—such as an electromagnetic signal in the visible light or infrared spectrum—when the corresponding promoter is activated. For example, the reporter in the sensor plant can be configured to fluoresce (i.e., produce a signal in the visible spectrum) when the corresponding promoter is active in the sensor plant. More specifically, a promoter-reporter pair can be incorporated into the sensor plant via molecular binding and metabolic engineering techniques that associate expression of a promoter responsive to a particular biological stress with a reporter that produces a measurable signal when the promoter expresses. The promoter-reporter pair can be configured to produce a measurable signal by pairing the reporter with the promoter, such that when the promoter expresses the reporter also expresses. Therefore, via expression of the reporter, the promoter-reporter pair can produce a measurable signal of a particular biological stress or trait in the sensor plant.

1.3.1 Multiple Promoter-Reporter Pairs

In one variation, the sensor plant can be genetically modified to include multiple promoter-reporter pairs, each promoter-reporter pair indicative of a particular biological process occurring in the sensor plant cells in response to a particular stressor. For example, the sensor plant can include: a first promoter-reporter pair including a first promoter representative of a first biological process linked to presence of a water stressor tagged to a red fluorescence protein reporter; and a second promoter-reporter pair including a second promoter representative of a second biological process linked to presence of a fungi stressor tagged to a yellow fluorescence protein reporter. Then, in response to presence of a fungi stressor in the sensor plant, the sensor plant can: initiate the second biological process, and therefore express the second promoter; express the yellow fluorescence protein reporter; and signal a fungi stressor magnitude above a threshold fungi stressor magnitude. Therefore, the sensor plant can signal presence of multiple stressors via genetic modification of the sensor plant cells to include a set of promoter-reporter pairs.

In this variation, the computer system can distinguish between different signals from the sensor plant to determine which stressor is present in the sensor plant. For example, the computer system can: access an image of the sensor plant; access a reporter model linking characteristics of the image of the sensor plant to a particular stressor (e.g., yellow fluorescence signals a fungal pressure); identify a presence of the particular stressor in the sensor plant based on the reporter model; and alert a farmer of the particular stressor in the sensor plant.

In another example, the sensor plant is genetically modified to include a set of promoters, wherein each promoter is representative of a unique biological process that occurs in response to a presence of a particular stressor in the sensor plant. In this example, the sensor plant is genetically modified to include a set of promoters including: a first promoter configured to activate in the presence of an insect pressure; a second promoter configured to activate in the presence of a fungal pressure; and a third promoter configured to activate in the presence of a water-related pressure (e.g., too much and/or too little water). Each promoter in this set of promoters can be paired with a unique reporter—in a set of reporters—in the sensor plant to form three promoter-reporter pairs in the sensor plant. In particular: first promoter can be paired with a first reporter configured to express a red fluorescence protein; the second promoter can be paired with a second reporter configured to express a yellow fluorescence protein; and the third promoter can be paired with a third reporter configured to express a green fluorescence protein. Then, the computer system can: access an image of the sensor plant, the image collected by a digital spectrometer; access a reporter model linking expression of fluorescent proteins (e.g., red, yellow, green) as visible in the image of the sensor plant to plant stressors (e.g., red fluorescence signals an insect pressure); in response to characteristics of the image of the sensor plant displaying yellow fluorescence, identify a fungal pressure at the sensor plant; and prompt a farmer of the fungal pressure in the sensor plant. Additionally, the computer system can link the fungal pressure to a particular action in a set of possible actions, and prompt a farmer of the crop to apply fungicide to an infected area to mitigate the fungal pressure.

1.3.2 Combinatorial Promoter-Reporter Pairs

In one variation, the sensor plant can be genetically modified to include a multiplexed gene sensing network representative of a set of combinatorial promoter-reporter pairs. The multiplexed gene sensing network includes multiple promoters tied to one or more reporters. The sensor plant can therefore include a set of promoters, each promoter in the set of promoters paired to a reporter in a set of reporters or a combination of these reporters. For example, the sensor plant can be genetically modified to include: a first promoter paired to a red fluorescing reporter, the first promoter linked to a first biological process associated with a water stressor; a second promoter paired to a yellow fluorescing reporter, the second promoter linked to a second biological process associated with a fungal stressor; and a third promoter paired to both the red fluorescing reporter and the yellow fluorescing reporter, the third promoter linked to a third biological process associated with a heat stressor. In response to the plant cell exceeding a threshold temperature, the sensor plant can: initiate the third biological process, and therefore express the third promoter; express the red fluorescing reporter and the yellow fluorescing reporter; and signal presence of a heat stressor in the plant (e.g., sensor plant temperature above a threshold temperature).

Therefore, the sensor plant can be genetically modified to include this multiplexed gene sensing network to leverage a set of reporters to detect expression of a set of promoters linked to particular biological processes that occur in the plant. Thus, the sensor plant can leverage a small number of reporters (e.g., fluorescing compounds) to monitor and detect a greater number of promoters and/or biological processes and therefore simplify the detection process by reducing the number of reporters required, as fluorescent compounds exhibit broad spectral features and may be difficult to simultaneously measure and distinguish between a large number of these fluorescent compounds.

1.4 Linked Promoter-Reporter Pairs

In one variation, the sensor plant includes a set of promoter-reporter pairs, each: configured to express a unique signal in the presence of a unique primary pressure; and configured to modify expression of its unique signal in the presence of a secondary pressure.

In one example, the sensor plant can be genetically modified to include: a first promoter-reporter pair that expresses in a presence of a water stressor; and a second promoter-reporter pair that expresses in a presence of a fungal stressor. Thus, in response to presence of the fungal stressor, the sensor plant can: increase expression of the second promoter-reporter pair to signal presence of the fungal stressor. However, the sensor plant may deactivate the first promoter-reporter pair in the course a natural response to this fungal stressor.

Therefore, in this example, the computer system can: access a sequence of images of this sensor plant captured over a period of time; detect presence of the fungal stressor at the sensor plant based on increased intensity of a second signal associated with expression of the second promoter-reporter pair over this sequence of images; and confirm presence of the fungal stressor based on decreased intensity of a first signal associated with expression of the first promoter-reporter pair over this sequence of images. If, however, the computer system detects no change in magnitude of expression of the first promoter-reporter pair concurrently with an increase in magnitude of expression of the second promoter-reporter pair, then the computer system can interpret a different stressor on the sensor plant. For example, if the second reporter in the sensor plant is also linked to a third promoter for a third stressor (e.g., nutrient deficiency) that does not affect expression of the first reporter-promoter pair, the computer system can interpret presence of the third stressor at the sensor plant in response to no detected change in magnitude of expression of the first promoter-reporter pair concurrently with an increase in magnitude of expression of the second promoter-reporter pair.

Therefore, the sensor plant can be configured to include promoter-reporter pairs that signal presence of particular stressors in the sensor plant and additionally alter expression of this signal in the presence of a different stressor not associated with a particular promoter-reporter pair. Thus, the computer system can: access images of the sensor plant; identify a particular stressor presence in the sensor plant based on characteristics of the images; and confirm the particular stressor presence in the sensor plant based on signals produced by other promoter-reporter pairs in the sensor plant or in nearby sensor plants matching predicted promoter-reporter pair expression in the presence of the particular stressor.

1.5 Linking Reporters to Courses of Action

In another variation, the sensor plant can include: a first promoter that expresses in presence of a water stressor paired to a red fluorescence protein reporter to generate a first promoter-reporter pair; and a second promoter that expresses in presence of a heat stressor paired to a red fluorescence protein reporter to generate a second promoter-reporter pair. Then, in response to a water concentration of the sensor plant falling below a minimum threshold water concentration (e.g., due to a hot dry day), the sensor plant can generate a red fluorescent signal for detection of the water stressor. Additionally and or/alternatively, in response to a temperature of the sensor plant exceeding a maximum threshold temperature, the sensor plant can generate the red fluorescent signal for detection of the heat stressor. The computer system can: detect a stressor via images of the sensor plant; access a reporter model linking features of the images to stressors; identify the stressor as either a water stressor or a heat stressor; and prompt a farmer to irrigate the sensor plant and the surrounding plants or crop. Therefore, the computer system can leverage understanding that multiple stressors may be mitigated or treated with the same course of action to pair promoters representative of different biological processes or stressors to the same reporter or signal.

Therefore, the sensor plant can include one reporter linked to multiple promoters configured to activate in the presence of different stressors that may be addressed and ameliorated with the same course of action. Furthermore, the computer system can: detect one signal expressed by the reporter in the presence of any pressure that activates a promoter linked to the reporter; and output a recommendation for a course of action linked to this reporter and that, accordingly, may address any of the possible stressors present at the sensor plant.

1.6 Reporter Signaling Duration

In one variation, the sensor plant can be genetically modified to include multiple promoters linked to a particular biological process (or similar biological processes) and paired with a single reporter to increase a duration over which the reporter is expressed. For example, a sensor plant can be genetically modified to include a set of promoters paired to one reporter, each promoter in the set of three promoters linked to a biological process that occurs in the plant cells in response to presence of a water stressor. Each of these promoters can be selected and/or configured to express at different times while the biological process is active.

For example, in response to a sensor plant water concentration falling below a minimum water concentration, the sensor plant can: at a first time, initiate a particular biological process linked to plant cell dehydration; express a first promoter in the set of promoters; and express the reporter for a first duration, signaling low water concentration in the sensor plant. Then, at a second time immediately preceding a termination of the first duration, the sensor plant can: continue activation of the particular biological process; express a second promoter in the set of promoters; and express the reporter for a second duration. Therefore, by pairing multiple promoters linked to a single biological process with a single reporter, the sensor plant can increase a total duration over which a reporter is expressed, thus increasing a window of detection during which the sensor plant can signal presence of a stressor in the sensor plant.

In a similar example, the sensor plant is genetically modified to include a set of promoters, wherein each promoter exhibits promoter activity representative of the same native biological process that occurs in the presence of an insect pressure but is configured to activate within a different time interval of the native biological process. In this example, a first promoter in the sensor plant can be configured to exhibit this promoter activity for the first day of an insect pressure above a constitutive insect pressure; and a second promoter in the sensor plant can be configured to exhibit this promoter activity for the second and third days of an insect pressure above the constitutive insect pressure; etc. Furthermore, this set of promoters can be paired to the red fluorescence protein reporter described above. Therefore, in the presence of an insect pressure over a period of time, the set of promoters can activate (approximately) consecutively throughout this time period, and the red fluorescence protein reporter can continue to express—in the form of a measurable signal—during this time period as these promoters (approximately) consecutively activate and deactivate. Therefore, the sensor plant can exhibit red fluorescence responsive to this insect pressure over an extended duration of time, thereby increasing a window of time that this signal is measurable in the sensor plant and thus extending a window of time in which a farmer, agronomist, or other entity may capture an image of the sensor plant that the computer system can then interpret into presence of this insect pressure. In particular, the computer system can then: access an image of this sensor plant; detect this signal—produced via expression of this reporter responsive to activation of one of these promoters—in this image of the sensor plant; identify presence of the insect pressure in the plant based on intensity of the signal thus detected in this image; and alert the farmer or agronomist of the insect pressure accordingly. The computer system can additionally or alternatively serve a prompt to the farmer or agronomist to execute a particular course of action to mitigate this insect pressure, such as if the intensity of the signal thus detected in this image exceeds a threshold intensity.

1.7 Stressor Magnitude

In one variation, the sensor plant can generate signals of different magnitudes based on the magnitude of corresponding stressor pressures. For example, a sensor plant can be genetically modified to include a promoter-reporter pair configured to express a red fluorescent protein in response to a fungal pressure presence in the sensor plant. In response to the fungal pressure exceeding a minimum fungal pressure threshold, the sensor plant can express the fluorescence protein to generate a fluorescent signal above a threshold intensity. In response to a fungal pressure exceeding a minimum fungal pressure threshold and falling below an intermediate fungal pressure threshold, the sensor plant can express the fluorescence protein to generate a low level signal. Alternatively, in response to the fungal pressure exceeding the intermediate fungal pressure threshold, the sensor plant can express the fluorescence protein to generate a high level signal.

The computer system can distinguish different magnitudes of stressor pressures based on the signal generated by the sensor plant and therefore prompt a particular course of action based on the magnitude of stressor pressure in the sensor plant. In one variation, the computer system can determine whether a sensor plant signal associated with a particular stressor exceeds a signal threshold and then prompt a farmer to perform a particular course of action associated with the stressor at a particular magnitude. For example, the computer system can: detect expression of a particular promoter-reporter pair via images of a sensor plant genetically modified to include the particular promoter-reporter pair; in response to expression of the particular promoter-reporter pair, measure a wavelength of fluorescence of the sensor plant corresponding to a particular magnitude; and in response to the particular magnitude falling above a threshold magnitude, prompt a farmer to perform a course of action (e.g., "apply fungicide") in order to mitigate or treat a stressor pressure (e.g., a fungal pressure).

In one variation, the sensor plant can generate signals of different magnitudes based on the magnitude of corresponding stressor pressures. For example, a sensor plant can be genetically modified to include a promoter-reporter pair configured to express a fluorescent protein in response to a fungal pressure presence in the sensor plant. In response to a fungal pressure exceeding a minimum fungal pressure threshold and falling below an intermediate fungal pressure threshold, the sensor plant can express the fluorescence protein to generate a low level signal at a first wavelength. Alternatively, in response to the fungal pressure exceeding the intermediate fungal pressure threshold and falling below a maximum fungal pressure threshold, the sensor plant can express the fluorescence protein to generate an intermediate level signal at a second wavelength. Alternatively, in response to the fungal pressure exceeding the maximum fungal pressure threshold, the sensor plant can express the fluorescence protein to generate a high level signal at a third wavelength.

The computer system can distinguish different magnitudes of stressor pressures based on the signal generated by the sensor plant and therefore prompt a particular course of action based on the magnitude of stressor pressure in the sensor plant. For example, the computer system can: at a first time, measure a first wavelength of a sensor plant via images of the sensor plant; access a reporter model linking wavelengths of sensor plants to magnitudes of stressor pressures; and calculate a first magnitude of a stressor pressure at the first wavelength. Then, at a second time, the computer system can measure a second wavelength of the sensor plant and access the reporter model to calculate a second magnitude of the stressor pressure at the second wavelength.

In one variation, the computer system can prompt a particular course of action in response to the detection of a pressure magnitude above or below a threshold pressure magnitude. For example, the computer system can: at a first time, measure a first wavelength of a sensor plant via images of the sensor plant; access a reporter model linking wavelengths of sensor plants to magnitudes of stressor pressures; and calculate a first magnitude of a stressor pressure at the first wavelength. Then, in response to the first magnitude falling above a stressor pressure magnitude, the computer system can inform a farmer of the stressor pressure and the corresponding magnitude, and prompt the farmer to perform a particular course of action (e.g., "irrigate the crop").

1.8 Constitutive Reporter

In one variation, a sensor plant can be genetically modified to include a constitutive promoter-reporter pair to account for external factors (e.g., temperatures, pH levels)

affecting promoter and reporter expression. For example, an increase in plant temperature may reduce the magnitude of a fluorescence signal generated by sensor plants. To account for this decrease in magnitude of the signal, a sensor plant can be genetically modified to generate a constitutive sensor plant that can generate a signal unresponsive to changes in stressor but responsive to external factors. In one implementation, the sensor plant can be genetically modified to include: a constitutive promoter representative of a native biological process that occurs in the sensor plant continuously, regardless of any stressor; and a constitutive reporter paired to the promoter to generate a constitutive promoter-reporter pair. The sensor plant can express the constitutive promoter and therefore the constitutive reporter both in the absence and presence of stressors. The computer system can then measure a magnitude of a signal produced by the sensor plant and record the magnitude as a constitutive magnitude for this particular constitutive reporter.

For example, a sensor plant can be genetically modified to include: a constitutive promoter representative of a native biological process that occurs in plants at all times; and a constitutive reporter that, when expressed, generates a red fluorescent signal, the constitutive reporter paired to the constitutive promoter to form a constitutive promoter-reporter pair. Additionally, a second sensor plant can be genetically modified to include: a promoter representative of a biological process that occurs in plants in the presence of a fungal pressure; and a reporter that, when expressed, generates the red fluorescent signal, the reporter paired to the promoter to form a promoter-reporter pair. The constitutive sensor plant can generate a continuous red fluorescent signal that may alter in magnitude in response to various external factors or environmental conditions, but not in response to a fungal pressure. When a fungal pressure is present, the second sensor plant can express the promoter-reporter pair and generate a signal with a first magnitude. The computer system can then: access images of both the second sensor plant and the constitutive sensor plant; measure wavelengths of both the first signal and the constitutive signal; calculate a difference between the first signal and the constitutive signal to estimate a relative magnitude of the first signal for the second sensor plant. Then, the computer system can determine a particular course of action based on the relative magnitude of the fungal pressure and prompt a farmer to perform this course of action. Therefore, the computer system can account for external factors (e.g., not related to the particular stressor associated with the promoter-reporter pair) that cause changes in the reporter signal when identifying magnitudes of stressor pressures and determining the appropriate course of action.

In one variation, sensor plants can include a constitutive promoter-reporter pair representative of a biological process that occurs in plants naturally in order to identify weeds and/or other invasive plant species in a crop. For example, a sensor plant can include a constitutive promoter-reporter pair that produces a constitutive signal (e.g., an optical signal) at all times. The computer system can detect this constitutive signal in an image of the crop and identify the sensor plant and other plants naturally producing this signal as crop plants accordingly. However, in response to failure to detect the constitutive signal and/or in response to detecting the constitutive signal at an intensity less than a threshold signal intensity in an image of the crop, the computer system identify a weed(s) in the crop and alert a farmer of a weed presence in the crop accordingly.

1.9 Sensor Plant Clusters

Sensor plants can be planted in crops of plants (e.g., crops of corn, crops of soybeans, etc.) to signal stressor pressures present in the crop. In one variation, multiple sensor plants can be planted in a cluster in designated sensor plant regions in the field, such as in specific crop rows (e.g., every $50^{th}$ crop row) or in target segments of crop rows (e.g., three-row-wide, three-meter-long clusters with a minimum of 20 crop rows or 20 meters between adjacent clusters of sensor plants). By planting multiple sensor plants in clusters within a crop, a cluster of sensor plants can produce a cumulative signal characterized by a greater signal-to-noise ratio than a lone sensing plant.

In one variation, neighboring sensor plants can be genetically modified to include the same promoter-reporter pairs to increase magnitude of a cumulative signal of the sensor plants. For example, a first sensor plant can be genetically modified to include a promoter-reporter pair configured to signal presence of an insect pressure within a crop. The first sensor plant can be planted within a row of sensor plants—each genetically modified to include the same promoter-reporter pair—within a crop. In response to a migration of an insect pressure across the crop, the row of sensor plants—including the first sensor plant—can produce a cumulative signal to indicate presence of the insect pressure. Therefore, by planting sensor plants in a cluster (e.g., row), this cluster of sensor plants may also yield greater spatial information regarding direction and scope of a stressor pressure moving across the crop (e.g., an insect pressure migrating across the crop) than a lone sensor plant.

In one variation, a sensor plant can be genetically modified to include a different promoter-reporter pair than a neighboring sensor plant in a cluster of sensor plants. For example, a cluster of sensor plants can include: a first sensor plant genetically modified to include a first promoter-reporter pair, the first promoter-reporter pair configured to signal presence of an insect pressure in the first sensor plant; and a second sensor plant genetically modified to include a second promoter-reporter pair, the second promoter-reporter pair configured to signal presence of a fungi pressure in the second sensor plant. In response to detecting an insect pressure, the first sensor plant can signal presence of the insect pressure by expressing the first promoter-reporter pair to generate a detectable signal (e.g., fluorescent light). Additionally or alternatively, in response to detecting a fungi pressure, the second sensor plant can signal presence of the fungi pressure by expressing the promoter and reporters to generate a detectable signal (e.g., fluorescent light). The computer system can then: detect these signals via previously recorded or near real-time images of these sensor plants; access a reporter model linking sensor plant signals to stressor pressures to identify the stressor pressure signaled by each sensor plant; and, in response to identifying the stressor pressure, identify a particular course of action based on the stressor pressure; and prompt a farmer or crop manager to perform the particular course of action in order to mitigate the stressor pressure. Therefore, by planting clusters of sensor plants including different promoter-reporter pairs, the computer system can: detect signals (e.g., presence) of multiple pressures; simplify identification of stressor pressures (e.g., if each sensor plant includes one promoter-reporter pair); and simplify image collection of the sensor plants and therefore detection of these stressor pressures by grouping sensor plants together in specific regions of a crop.

1.10 Sensor Plants in Cover Crops

In one implementation, sensor plants can be genetically modified to include: GMO plant genes within a GMO stack already present in GMO seeds; and promoter-reporter pairs configured to signal the presence of stressors within the GMO crop. These sensor plants may then be planted to produce an entire crop of sensor plants. In one variation, sensor plants can be planted as a cover crop (e.g., grasses, rye, wheat) that is planted between regular crop rotations. Sensor plants can be genetically modified to include promoter-reporter pairs configured to monitor soil health by sensing changes in soil health indicators such as: salinity, pH, nutrient density, nematodes, organic matter, etc. The sensor plants may then be planted between regular crop rotations (e.g., during winter) to produce a cover crop configured to signal soil health. For example, sensor plants in a cover crop can be genetically modified to include promoter-reporter pairs configured to signal a pH level below a minimum pH level and/or above a maximum pH level. In response to detecting a low pH level below a minimum pH level, sensor plants can signal the low pH level by expressing the promoter and reporters to generate a detectable signal (e.g., fluorescent light). The computer system can then detect these signals via recorded images of the sensor plants; access a reporter model linking sensor plant signals to stressor pressures to identify the stressor pressure signaled by each sensor plant; and, in response to identifying a low pH signal, identify a particular course of action based on the low pH level; and prompt a farmer or crop manager to apply an agricultural lime to soil to raise the pH level of the soil in preparation for their next crop rotation. Additionally, the computer system can prompt the farmer to perform an additional course of action when regular crops are planted, based on soil health as signaled by the cover crop before the regular crop is planted. Therefore, sensor plants can be planted during "off-seasons" or in between regular crops to monitor soil conditions and prompt farmers to execute particular courses of action in order to improve soil conditions in preparation for planting regular crops based on soil conditions as monitored by the sensor plants.

2. Second Method

Figure 3A:
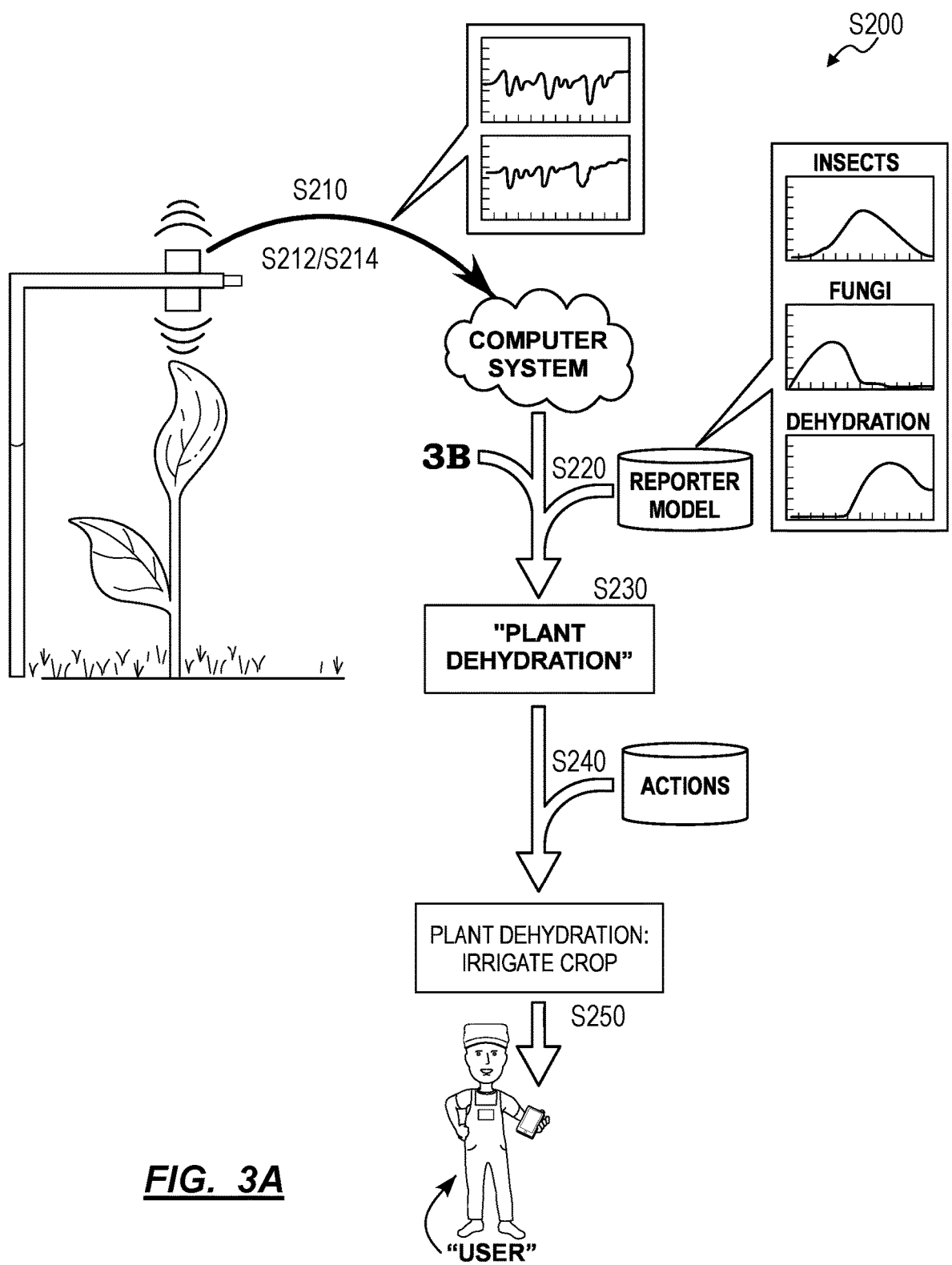
FIGS. 3A-3C are a flowchart representation of a second method.

As shown in FIG. 3A, a second method S200 for identifying stressors in crops based on fluorescence of sensor plants includes: accessing a set of spectral images of a sensor plant sown in a crop in Block S210, the sensor plant of a sensor plant type including a set of promoters and a set of reporters configured to signal a set of stressors present at the sensor plant, the set of promoters and set of reporters forming a set of promoter-reporter pairs; accessing a reporter model linking characteristics extracted from the spectral image of the sensor plant to the set of stressors based on signals generated by the set of promoter-reporter pairs in the sensor plant type in Block S220; and identifying a first stressor, in the set of stressors, present at the sensor plant based on the reporter model and characteristics extracted from the set of spectral images in Block S230.

Figure 3B:
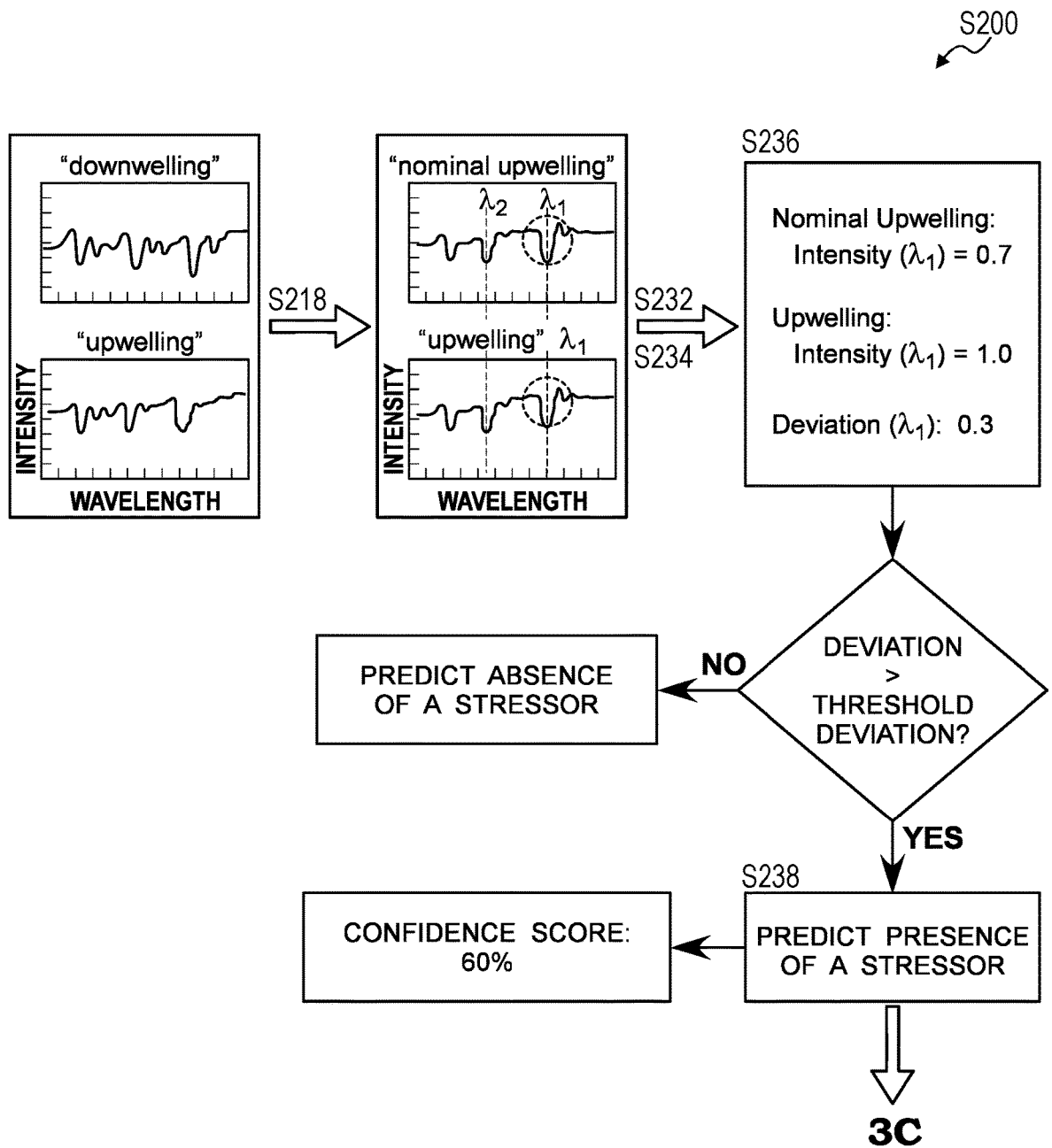

In one variation, as shown in FIG. 3B, the second method S200 further includes: estimating a nominal upwelling light spectrum based on the downwelling light spectrum represented in the first spectral image in Block S218, the nominal upwelling light spectrum representing reflectance and fluorescence of the sensor plant, absent the first stressor, in the presence of light according to the downwelling light spectrum at the first time. In this variation, identifying the first stressor in Block S230 includes: extracting a first intensity, at a first wavelength, in the upwelling light spectrum represented in the second spectral image in Block S232; extracting a first nominal intensity, at the first wavelength, in the nominal upwelling light spectrum in Block S234; calculating a first deviation between the first intensity and the first nominal intensity at the first wavelength in Block S236; and, in response to the first deviation exceeding a threshold deviation, predicting presence of the first stressor at the sensor plant in Block S238.

In one variation, as shown in FIG. 3A, the second method S200 further includes: isolating a first action, in a set of actions defined for the sensor plant type, linked to the first stressor in Block S240; and in response to identifying the first stressor, prompting a farmer to perform the first action at the crop to mitigate the first stressor in Block S250.

In one variation, the second method S200 includes: accessing a first spectral image of a sensor plant sown in a crop in Block S212, the first spectral image depicting a downwelling light spectrum and captured, at a first time, by an optical spectrometer defining a field of view facing opposite the sensor plant, the sensor plant of a sensor plant type configured to signal a set of stressors present at the sensor plant; accessing a second spectral image of a sensor plant sown in a crop in Block S214, the second spectral image depicting an upwelling light spectrum captured at approximately the first time, by the optical spectrometer defining the field of view facing the sensor plant; accessing a reporter model linking solar induced fluorescence measurements, extracted from the downwelling light spectrum and the upwelling light spectrum of the sensor plant, to the set of stressors for plants of a type of the sensor plant in Block S220; and identifying a first stressor, in the set of stressors, present at the sensor plant based on the reporter model and solar induced fluorescence measurements in Block S230.

2.1 Applications

Generally, a system—such as a local or remote computer system in conjunction with a user (e.g., technician, scientist, laboratory)—can execute Blocks of the second method S200 to identify a stressor present at a sensor plant (and therefore present within a greater planted crop more generally) based on signals (e.g., fluorescence in the electromagnetic spectrum) produced by the sensor plant, which is genetically modified to include a promoter-reporter pair configured to activate and exhibit a signal (e.g., fluorescence) in the presence of a particular stressor. More specifically, the computer system can: access hyperspectral images—of a leaf area of a sensor plant, a whole sensor plant, a group of like sensor plants, a whole crop of sensor plants, or many fields of sensor plants—recorded by a remote sensing system (e.g., in a handheld device, in a boom or pole installed in the field, in manned or unmanned field equipment, in an aircraft, or in a satellite); extract spectral characteristics for these hyperspectral images; and interpret presence and/or magnitude of a particular stressor(s) present at the sensor plant, group of plants, crop, or fields based on correlations between spectral characteristics extracted from these hyperspectral images and known characteristics (e.g., fluorescence) expressed by a particular generic promoter-reporter pair in this sensor plant.

Figure 6:
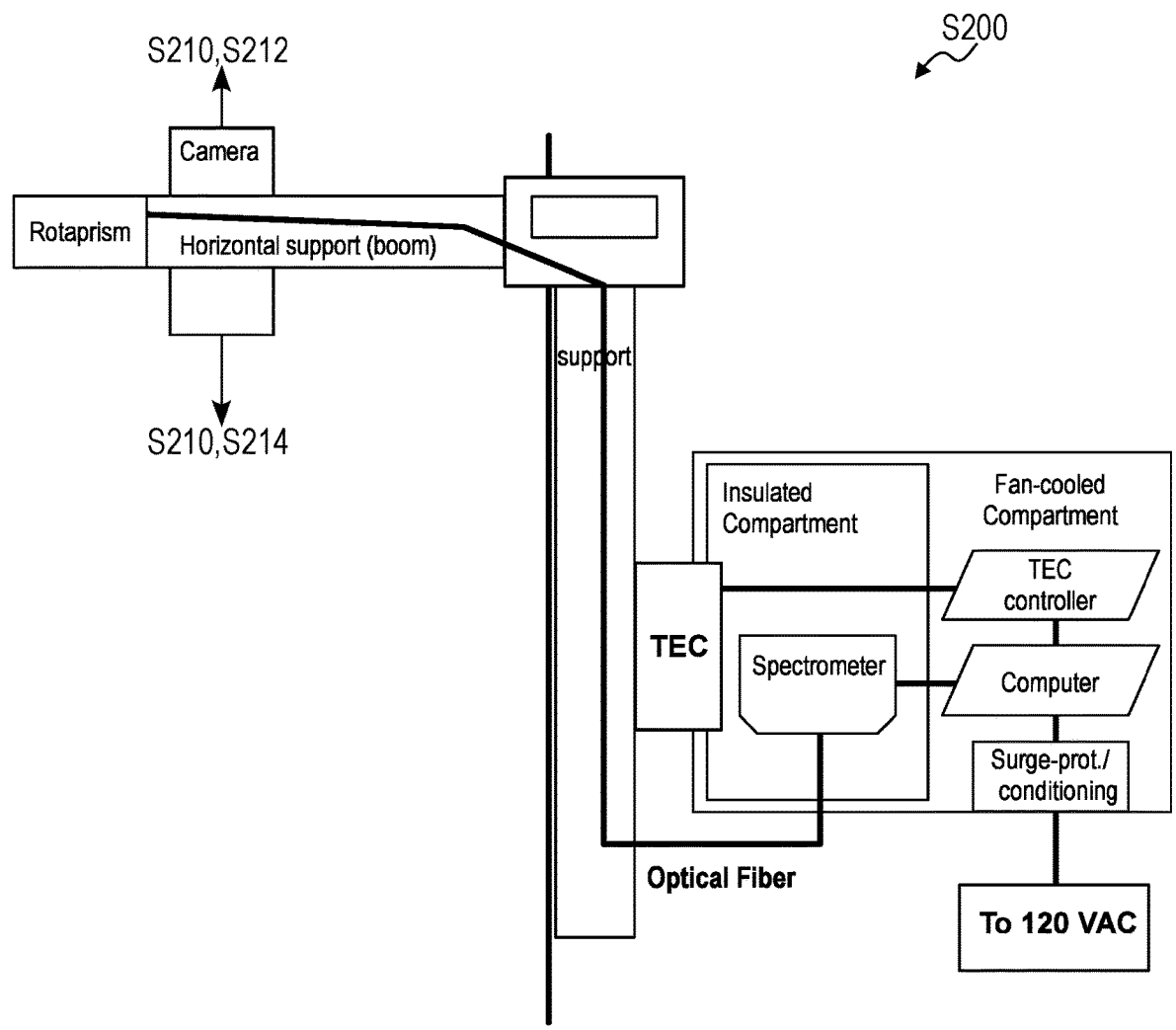
FIG. 6 is a schematic representation of a remote sensor system.

For example, the computer system can access a downwelling hyperspectral image representing a downwelling light spectrum (i.e., solar radiation radiated downward onto land) and an upwelling hyperspectral image representing an upwelling light spectrum (i.e., electromagnetic radiation reflected upwardly and electromagnetic radiation fluoresced by earth, plants, and other biomass), both recorded approximately concurrently by: a mobile handheld device including a hyperspectral sensor; a fixed or mobile ground-based hyperspectral sensor (e.g., mounted to a boom or pole installed in a field); a hyperspectral sensor arranged in an aircraft; or a satellite including a hyperspectral sensor. In a similar implementation, an imaging system (e.g., an RGB camera, a multispectral or hyperspectral imaging system) can capture digital images (e.g., RGB images, spectral images, hyperspectral images, multispectral images) of a plant canopy, such as including exclusively sensor plants or a combination of both sensor plants and nearby non-sensing plants. For example, the imaging system can include: an optomechanical fore optic that supports measurement of fluorescent and non-fluorescent targets; and a digital spectrometer sensor or digital camera sensor that records images through the optomechanical fore optic, as shown in FIG. 6. The imaging system can also: capture electromagnetic radiation inbound from opposing directions (e.g., upward to capture downwelling solar radiation and downward to capture upwelling reflected and fluoresced radiation) in one hyperspectral image; and then split this hyperspectral image into discrete, concurrent downwelling and upwelling hyperspectral images. Alternatively, the imaging system: can include an electromechanical motion system configured to rapidly change the field of view of the digital spectrometer sensor; can capture a downwelling hyperspectral image; and can then trigger the electromechanical motion system to capture an upwelling hyperspectral image soon after capturing the downwelling hyperspectral image.

The computer system can then: extract downwelling and upwelling spectral characteristics from these hyperspectral images; predict a nominal fluorescence spectrum of earth, plants, and biomass based on biology fluorescence models; and subtract the downwelling spectral characteristics and the nominal fluorescence spectrum from the upwelling spectral characteristics to calculate a composite spectrum that represents intensities of wavelengths of light likely fluoresced by a sensor plant(s) depicted in the upwelling hyperspectral image. The computer system can then: retrieve a reporter model that predicts a particular wavelength (or a narrow range of wavelengths) of electromagnetic radiation fluoresced by the sensor plant when a reporter gene in the sensor plant expresses responsive to activation of a linked promoter gene in the presence of a particular stressor; extract an intensity of electromagnetic radiation in the particular wavelength (or a narrow range of wavelengths)—of fluoresced electromagnetic radiation predicted by the reporter model—from the reporter model; and then transform this extracted intensity into a prediction of presence of the sensor plant represented in the upwelling hyperspectral image based on parameters in the reporter model (e.g., if the extracted intensity exceeds a threshold intensity defined by the reporter model). Additionally or alternatively, the computer system can transform this extracted intensity into a predicted magnitude of presence of the sensor plant based on this reporter model.

Thus, the computer system (e.g., a remote server, a local device, a computer network) can execute Blocks of the second method S200 to: access hyperspectral (or spectral) images of a sensor plant recorded by an imaging system; process these hyperspectral images to detect a signal expressed by a reporter gene in the sensor plant—but not visually discernible by a human—when triggered by a corresponding promoter gene activated by a particular stressor affecting the plant; and then interpret this signal as presence (and/or magnitude, duration) or absence of this particular stressor in this sensor plant, a cluster of plants; a crop; or a greater land area or geographic region. The computer system can then notify the user of presence (and/or magnitude, duration) of a detected stressor and/or prompt the user to execute a particular action in order to reduce or eliminate the stressor well before (e.g., weeks before) the stressor damages the sensor plant (and nearby plants) to a degree visually discernible by a human, at which time such damage may be otherwise irrecoverable and reduce or eliminate yield from this sensor plant (and/or nearby plants). For example, the computer system can transmit notifications or prompts directly to the user's mobile device (e.g., smartphone) or by writing notifications or prompts to an alert feed accessible to the user.

Therefore, the computer system can execute Blocks of the second method S200: to remotely detect early presence (and/or magnitude, duration) of a stressor at a particular sensor plant or at a group of plants, in a crop or field, in a land area or geographic region including one or more sensor plants; and to notify a user of presence of this stressor before this stressor substantively reduces viability or yield of this sensor plant, group, crop, or land area.

2.2 Promoter-Reporter Pair

A sensor plant can be genetically modified to include promoter and reporter pairs that indicate presence of stressors in the sensor plant. To detect presence of these stressors, a reporter that expresses a certain signal can be coupled to the promoter of choice, each promoter linked to a particular stressor. More specifically, the reporter can initiate a metabolic change in the sensor plant such that a detectable signal is produced (e.g., fluorescence). Therefore, when the sensor plant's cells express the promoter associated with a particular stressor, the reporter tagged to the promoter is also expressed and produces a detectable signal. For example, the sensing plant can be genetically modified to fluoresce (i.e., absorb photons at one frequency and emit photons at a different frequency) in the presence of (and proportional to) a disease or stressor. In this example, the sensing plant can be modified to fluoresce in the presence of one or more disease or other stress pressures, such as: fungi; bacteria; nematodes; parasites; viruses; insects; heat; water stress; nutrient stress; or phytoplasmal disease.

The promoter-reporter pair can be configured according to the third method S300 described below to produce a measurable signal by pairing the reporter with the promoter, such that when the promoter expresses the reporter also expresses. More specifically, in the presence of a particular stressor, the promoter gene can activate, thereby triggering the corresponding reporter to express a measurable signal (e.g., fluorescence) that is distinguishable by the computer system based on a comparison of downwelling solar radiation spectra and upwelling electromagnetic radiation spectra reflected by the sensor plant and other nearby biomass. Based on this measurable signal, the computer system can predict stressors present at sensor plants including the promoter-reporter pair. For example, the promoter-reporter pair can be configured to generate a fluorescence signal exhibiting a high signal-to-noise ratio to reduce effects of variations in downwelling solar radiation (e.g., due to clouds) and variations of biomass reflectance on stressor predictions. The computer system can thus access a set of hyperspectral images—depicting solar spectra (e.g., downwelling light spectra) and reflected and fluoresced light spectra (e.g., upwelling light spectra)—of the sensor plant, extract this signal (e.g., intensity of a particular wavelength or wavelength band in the electromagnetic spectrum) from this hyperspectral image, and interpret presence of this stressor based on this signal. For example, the computer system can extract fluorescence generated by the promoter-reporter pair from hyperspectral images (e.g., downwelling light spectra and upwelling light spectra) of the sensor plant. Based on the fluorescence signal generated by the sensor plant (e.g., wavelength and intensity of fluorescence), the computer system can identify a particular reporter associated with the fluorescence signal and therefore identify a particular promoter-reporter pair. Because the promoter is associated with a particular stressor, the computer system can identify a particular stressor present at the sensor plant as signaled by the sensor plant.

In one example, the computer system can access (e.g., via a computing device associated with the user) a set of hyperspectral images of a sensor plant genetically modified to include: a first promoter-reporter pair, in a set of promoter-reporter pairs, configured to fluoresce, at a first intensity, at a first wavelength, in response to presence of the first stressor at the sensor plant; and a second promoter-reporter pair, in the set of promoter-reporter pairs, configured to fluoresce, at a second intensity, at a second wavelength, in response to presence of the second stressor at the sensor plant. In this example, the computer system can identify the first stressor present at the sensor plant based on fluorescence of the sensor plant, at the first intensity, at the first wavelength.

2.3 Solar Induced Fluorescence

A user (e.g., technician, scientist, laboratory) can genetically modify a sensor plant to generate solar induced fluorescence in the presence of particular stressors by genetically modifying the sensor plant to include promoter-reporter pairs. Fluorescence is a process in which photons are absorbed by molecules at one frequency and emitted by these molecules at a different frequency. In particular, solar induced fluorescence (or "SIF") in plants is the reemission, at a longer wavelength, of solar photons absorbed by pigments in a plant. A user can isolate solar induced fluorescence produced by a sensor plant in a crop of plants in order to identify stressors present at the sensor plant.

To measure fluorescence of a sensor plant, a user can extract solar induced fluorescence measurements from hyperspectral images captured by an optical spectrometer. Hyperspectral images may depict upwelling light spectra and/or downwelling light spectra. The computer system can extract features from these spectra to determine fluorescence of the sensor plant, and therefore to determine whether a stressor presence exists at the sensor plant.

Figure 7A:
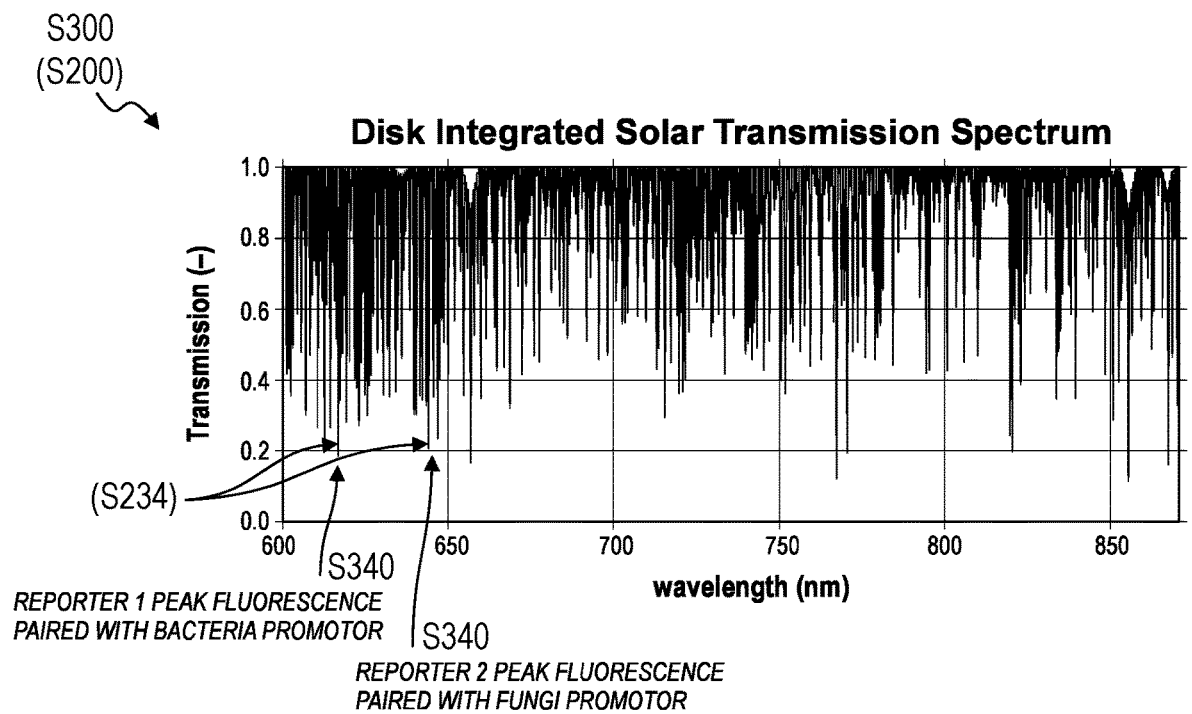
FIGS. 7A and 7B are graphical representations of solar spectra.
Figure 7B:
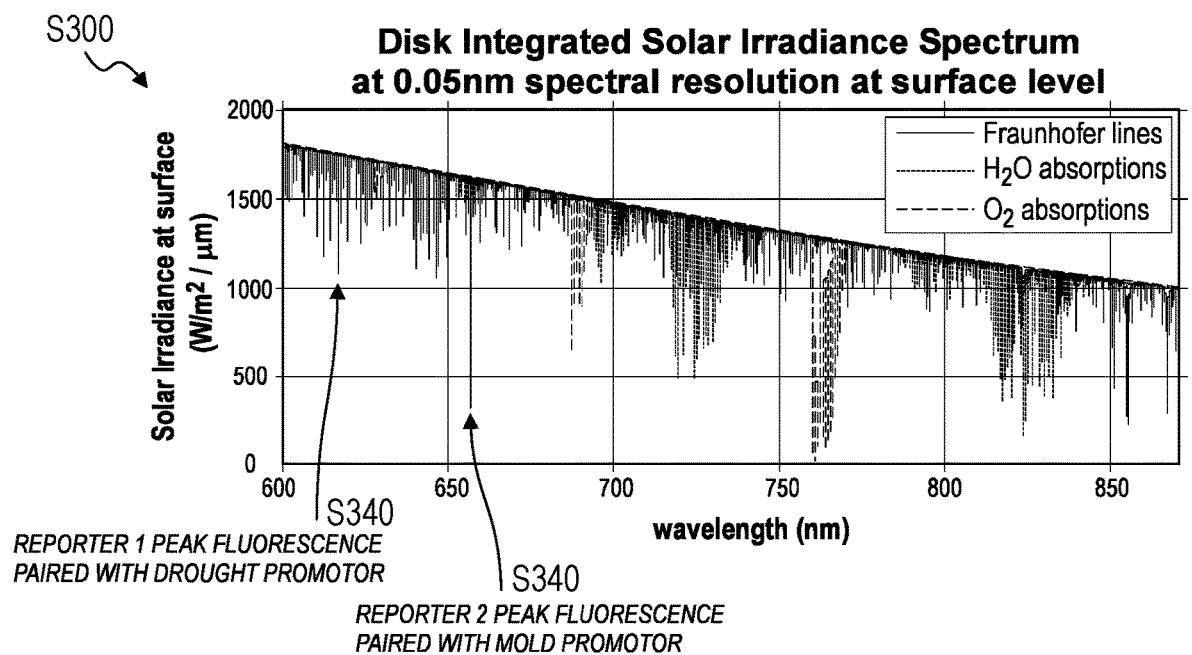

Fraunhofer lines represent wavelengths or narrow ranges of wavelengths at which the solar spectrum exhibits sharp decreases in intensity in the electromagnetic spectrum, as shown in FIGS. 7A and 7B. In one variation, the computer system can identify stressors present at the sensor plant based on changes in intensity at these Fraunhofer lines. Alternatively, the computer system can measure changes in intensity at Telluric lines. Therefore, at these wavelengths or wavelength bands (e.g. range of wavelengths), the computer system can distinguish between fluorescence generated by the sensor plant and other components of upwelling light.

2.3.1 Downwelling Light and Upwelling Light

A user can access hyperspectral images of a sensor plant in order to identify stressors present at the sensor plant. In particular, the computer system can access hyperspectral images depicting downwelling light spectra and upwelling light spectra of the sensor plant and extract characteristics of these spectra in order to identify stressors present at the sensor plant. A remote sensing system can capture these hyperspectral images depicting downwelling light and upwelling light at the sensor plant such that the computer system can remotely access these hyperspectral images via a computing device associated with the user for interpretation. For example, the computer system can access: a first hyperspectral image depicting a downwelling light spectrum and captured, at a first time, by an optical spectrometer defining a field of view opposite the sensor plant; and a second hyperspectral image depicting an upwelling light spectrum captured, at approximately the first time, by the optical spectrometer defining the field of view facing the sensor plant.

Figure 5A:
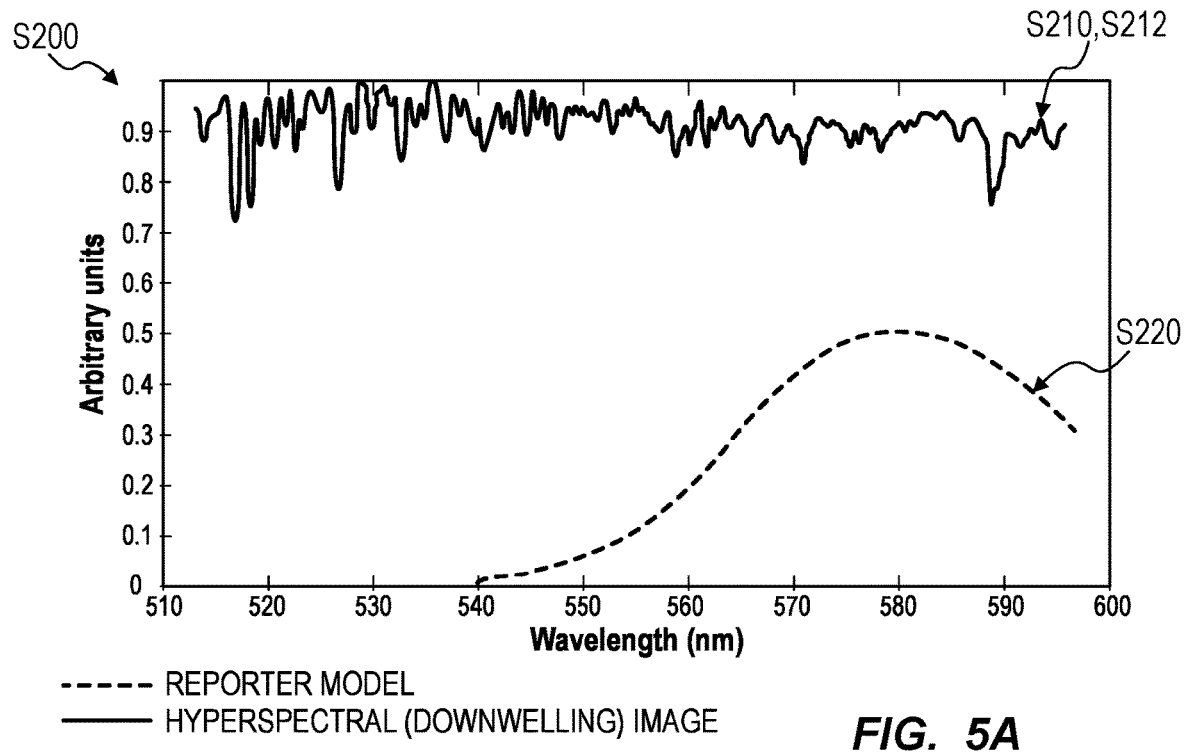
FIGS. 5A and 5B are graphical representations of wavelength spectra.
Figure 5B:
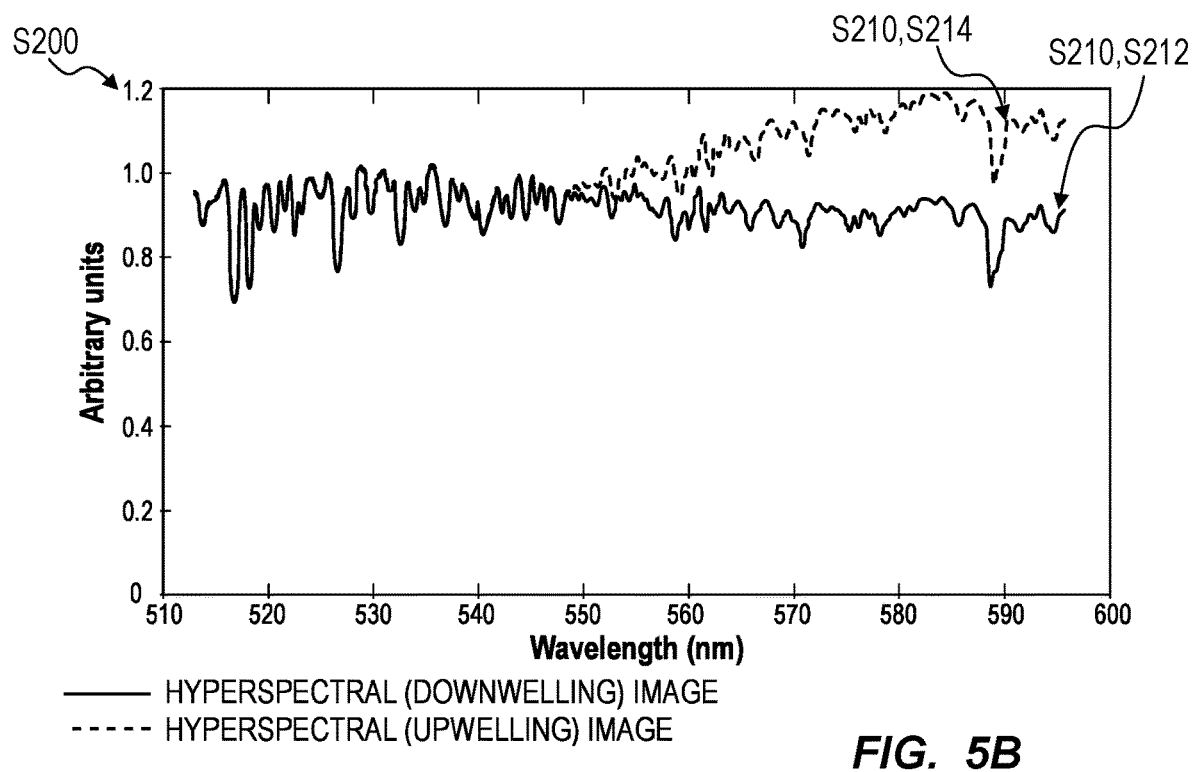

Downwelling light spectra captured above the sensor plant are representative of solar light incident at the sensor plant. As shown in FIG. 5A, downwelling light spectra (or "solar spectra") exhibit a fine spectral structure. Upwelling light includes light both reflected from and emitted by the sensor plant. Thus, upwelling light accounts for both reflected light and fluorescent light. As shown in FIG. 5B, upwelling light spectra exhibit a fine spectral structure, similar to the structure of the downwelling light spectrum.

Upwelling light includes both reflected light and fluorescent light. While reflected light spectra exhibit the fine spectral structure of the downwelling light, fluorescent light spectra are spectrally smooth. Reflected light is proportional to downwelling light. Therefore, reflected light spectra exhibit a similar shape to downwelling light spectra. However, fluorescent light exhibits a spectrally smooth shape, differing from the shape of downwelling light spectra and reflected light spectra. Therefore, the computer system can identify stressors present at the sensor plant based on differences in the shapes of the downwelling light spectrum and the upwelling light spectrum. The computer system can identify changes between the fine spectral structure of a particular upwelling light spectrum and downwelling light spectra to identify presence of a stressor at the sensor plant. For example, the computer system can: access a first hyperspectral image depicting a downwelling light spectrum and captured, at a first time, by an optical spectrometer defining a field of view facing opposite a sensor plant; access a second hyperspectral image depicting an upwelling light spectrum captured, at approximately the first time (e.g., within one second, five seconds, one minute, etc.), by the optical spectrometer defining the field of view facing the sensor plant; access a reporter model linking solar induced fluorescence measurements—extracted from downwelling light spectra and upwelling light spectra—to the set of stressors for plants of a type of the sensor plant; and identify a first stressor present at the sensor plant based on the reporter model and characteristics of the set of hyperspectral images. Thus, the computer system can identify fluorescence of the sensor plant based on differences between the downwelling light spectrum and the upwelling light spectrum, and therefore identify a stressor present at the sensor plant based on these differences.

Additionally and/or alternatively, the computer system can normalize downwelling light spectra and upwelling light spectra captured by the remote sensor system, and therefore extract normalized features (e.g., normalized intensities at particular wavelength ranges) from these spectra to identify stressors at the sensor plant, based on these normalized features.

In one variation, the user can identify changes in the upwelling light spectrum from the downwelling light spectrum by examining wavelength intensities of the spectra at Fraunhofer Lines in order to identify a stressor present at the sensor plant. For example, the computer system can: extract a normalized downwelling intensity, at a wavelength (or wavelength band) corresponding to a Fraunhofer line, from a downwelling spectrum depicted in a first hyperspectral image; extract a normalized upwelling intensity, at the wavelength (or within the range of wavelengths) corresponding to the Fraunhofer line in the electromagnetic spectrum, from an upwelling spectrum depicted in a second hyperspectral image; calculate a difference or ratio between the upwelling intensity and the downwelling intensity; and, in response to the difference exceeding a threshold difference, identify a first stressor present at the sensor plant.

In one implementation, the computer system can access an average downwelling light spectrum representative of a set of downwelling light spectra captured over a first set duration (e.g., one hour, six hours, twelve hours) and an average upwelling light spectrum representative of a set of upwelling light spectra captured over the set duration. The remote sensing system can capture images of the sensor plant at different angles and at different times throughout the day. In one implementation, the remote sensing system captures images of the sensor plant between 10 AM and 2 PM (e.g., when direct sunlight is maximized).

2.3.2 Nominal Upwelling Light

Upwelling light includes reflected light and fluorescence emissions. In the absence of fluorescence emissions (e.g., absence of a signaling sensor plant), upwelling light represents reflected light. Reflected light can be estimated as a fraction of downwelling light (e.g., 50%, 70%, 90%) at particular wavelengths based on reflectance of the sensor plant. Thus, in the absence of fluorescence, an upwelling light spectrum exhibits approximately the same structure as a corresponding (e.g., same location, time, day) downwelling light spectrum but with reduced intensities as a function of wavelength, accounting for absorbed and transmitted light (e.g., light that is not reflected).

A user can develop an upwelling light model for modelling upwelling light in the absence of fluorescence based on downwelling light measurements (e.g., intensity of light at various wavelengths). For example, a user can: access a first hyperspectral image depicting a downwelling light spectrum at a sensor plant and access a second hyperspectral image depicting an upwelling light spectrum recorded by a high-resolution spectrometer at a non-sensing plant of a first type; extract a reflected light spectrum and a baseline fluorescent light spectrum based on the downwelling light spectrum; calculate a reflectance factor based on the reflected light spectrum and the downwelling light spectrum; and generate an upwelling light model based on the reflectance factor and the baseline fluorescent light spectrum. The computer system can refine the upwelling light model by repeating this process for multiple downwelling light spectra and upwelling light spectra to calculate an average reflectance factor and/or average baseline fluorescence measurements. Later, the computer system can access this upwelling light model to generate nominal upwelling light spectra (e.g. expected upwelling light spectra in the absence of stressors) according to measured downwelling light spectra. Therefore, the computer system can compare upwelling light spectra to nominal upwelling light spectra (e.g., as estimated by the upwelling light model) to identify stressors present at the sensor plant.

In one implementation, the computer system can estimate nominal upwelling light spectra according to the following upwelling light model:

$$y(\lambda) = a \times r(\lambda) s(\lambda) + b \times f(\lambda) \qquad \text{(Equation 1)}$$

The computer system can estimate nominal upwelling light $y(\lambda)$ according to Equation 1, where $y(\lambda)$ represents the nominal upwelling light (or "expected upwelling light") predicted at the sensor plant in the absence of stressors, $r(\lambda)$ represents the canopy reflectance (e.g., reflectance of sensor plant and surroundings), $s(\lambda)$ represents measured downwelling light, $f(\lambda)$ represents canopy fluorescence (e.g., fluorescence of sensor plant and surroundings), and a and b are intensity factors.

In one variation, the computer system can generate an upwelling light model accounting for external factors included in images of the sensor plant such as other types of plants, soil, rocks, etc. For example, the computer system can access a set of hyperspectral images recorded from a satellite. In this example, the hyperspectral images may correspond to an entire crop rather than solely the sensor plant. Thus, the computer system can estimate nominal upwelling light, in the absence of the stressor, for the entire crop, based on types of plants, soil, and/or other features represented in the hyperspectral images.

Generally, the computer system can, at a first time, generate an upwelling light model. Later, the computer system can access the upwelling light model to check for differences between an upwelling light spectra recorded at the sensor plant and nominal upwelling light spectra, estimated by the upwelling light model and based on downwelling light spectra, in order to determine whether a pressure is present at a sensor plant of the first type. For example, the computer system can: access a downwelling light spectrum and an upwelling light spectrum of a sensor plant recorded by a high-resolution spectrometer; access the upwelling light model; estimate a nominal upwelling light spectrum based on the upwelling light model and the downwelling light spectrum; calculate a deviation between an area of the upwelling light spectrum between a first wavelength and a second wavelength (e.g., within a narrow range of wavelengths) and an area of the model upwelling light spectrum between the first wavelength and the second wavelength; and, in response to the deviation exceeding a threshold deviation, identify a particular stressor present at the sensor plant.

2.3.3 Extract Reporter Fluorescence

In one variation, the computer system can extract a solar induced fluorescence spectrum of a sensor plant from a downwelling light spectrum and an upwelling light spectrum recorded at the sensor plant in order to identify a particular stressor present at the sensor plant. For example, the computer system can: access an upwelling light spectrum recorded at the sensor plant, the upwelling light spectrum a combination of a reflected light spectrum and a measured fluorescent light spectrum; and extract a reporter fluorescent light spectrum based on the upwelling light spectrum and the downwelling light spectrum. In this example, the computer system can extract the reporter fluorescent light spectrum including: estimating the reflected light spectrum by multiplying the downwelling light spectrum by a reflectance factor; and estimating the measured fluorescent light spectrum as a first difference between the upwelling light spectrum and the reflected light spectrum;

and estimating the reporter fluorescent light spectrum as equivalent to the measured fluorescent light spectrum.

The computer system can further refine this reporter fluorescent light spectrum by accounting for fluorescence not produced by the sensor plant (e.g., fluorescence produced by other plants, soil, etc.). For example, the computer system can: access a model fluorescent light spectrum corresponding to total fluorescence within an area of the sensor plant; calculate a second difference between the measured fluorescent light spectrum and the model fluorescent light spectrum; and estimate the reporter fluorescent light spectrum for the sensor plant based on the difference.

Once the user has extracted the reporter fluorescent light spectrum, the computer system can identify a particular reporter associated with the reporter fluorescent light spectrum and therefore identify a particular promoter-reporter pair and particular stressor associated with the fluorescence signal produced by the sensor plant.

In one variation, the computer system can estimate reporter fluorescence from the upwelling light and downwelling light captured, approximately concurrently, of the sensor plant, based on Fraunhofer Lines, to predict stressor presence. The computer system can estimate reporter fluorescence as a difference between measured downwelling light and measured upwelling light. For example, the computer system can: extract a downwelling intensity from a first hyperspectral image depicting a downwelling light spectrum, at the wavelength associated with the Fraunhofer line in the electromagnetic spectrum; extract an upwelling intensity (e.g., a normalized upwelling intensity) from a second hyperspectral image depicting an upwelling light spectrum (e.g., a normalized upwelling light spectrum), at the wavelength associated with the Fraunhofer line in the electromagnetic spectrum; calculate a difference between the upwelling intensity and the downwelling intensity; and, in response to the difference exceeding a threshold difference, identify the first stressor present at the sensor plant. In this example, the computer system can estimate reporter fluorescence as equivalent to the difference between the upwelling intensity and the downwelling intensity.

In one variation, the computer system can estimate a reporter fluorescent light spectrum from the upwelling light spectrum and the downwelling light spectrum. For example, the computer system can: access a downwelling light spectrum and an upwelling light spectrum, the upwelling light spectrum representing a summation of a reflected light spectrum and a fluorescent light spectrum; and extract a reporter fluorescent light spectrum from the upwelling light spectrum. In this example, to extract the reporter fluorescent light spectrum, the computer system can: estimate the reflected light spectrum based on reflectance factors of the sensor plant, in the presence of light according to the downwelling light spectrum at the first time; estimate the fluorescent light spectrum based on a first difference between the upwelling light spectrum and the reflected light spectrum; and estimate the reporter fluorescent light spectrum as the fluorescent light spectrum. Alternatively, to refine the reporter fluorescent light spectrum, the computer system can: access a nominal fluorescent light spectrum representative of fluorescence within the area of the sensor plant absent the first stressor, in the presence of light according to the downwelling light spectrum at the first time; calculate a second difference between the fluorescent light spectrum and the nominal fluorescent light spectrum; and estimate the reporter fluorescent light spectrum for the sensor plant based on the difference. In this example, the computer system can account for fluorescence, captured in the upwelling spectrum depicted in the hyperspectral images, generated by external factors, such as other fluorescing plants and soil. Therefore, the computer system can extract the fluorescent light spectrum (e.g., total fluorescence) from the upwelling light spectrum, and then further extract the reporter fluorescent light spectrum (e.g., fluorescence initiated by the reporter in the sensor plant).

The computer system can access a reporter model linking fluorescence measurements of the sensor plant extracted from the set of hyperspectral images to a particular stressor. For example, the user can extract a first intensity, at a first wavelength, in an upwelling light spectrum depicted in a first hyperspectral image. The user can then access a reporter model linking the first intensity, at the first wavelength, to presence of a first stressor. In this example, the user can access the reporter model linking wavelength intensities to a particular stressor. In another example, the user can: extract a first intensity, at a first wavelength, in an upwelling light spectrum depicted in a first hyperspectral image; extract a first nominal intensity, at the first wavelength, in a nominal upwelling light spectrum representing reflectance and fluorescence of the sensor plant, absent the first stressor, in the presence of light; calculate a first deviation between the first intensity and the first nominal intensity at the first wavelength the reporter model linking; and, in response to the first deviation exceeding a threshold deviation, predict presence of a stressor at the sensor plant. The user can access the reporter model linking the first deviation to a particular stressor present at the sensor plant, based on characteristics (wavelength intensities) of fluorescence of the reporter. Therefore, the user can first determine presence of a stressor, and determine the particular stressor present based on the reporter model.

2.4 Predicting Stressors

Figure 3C:
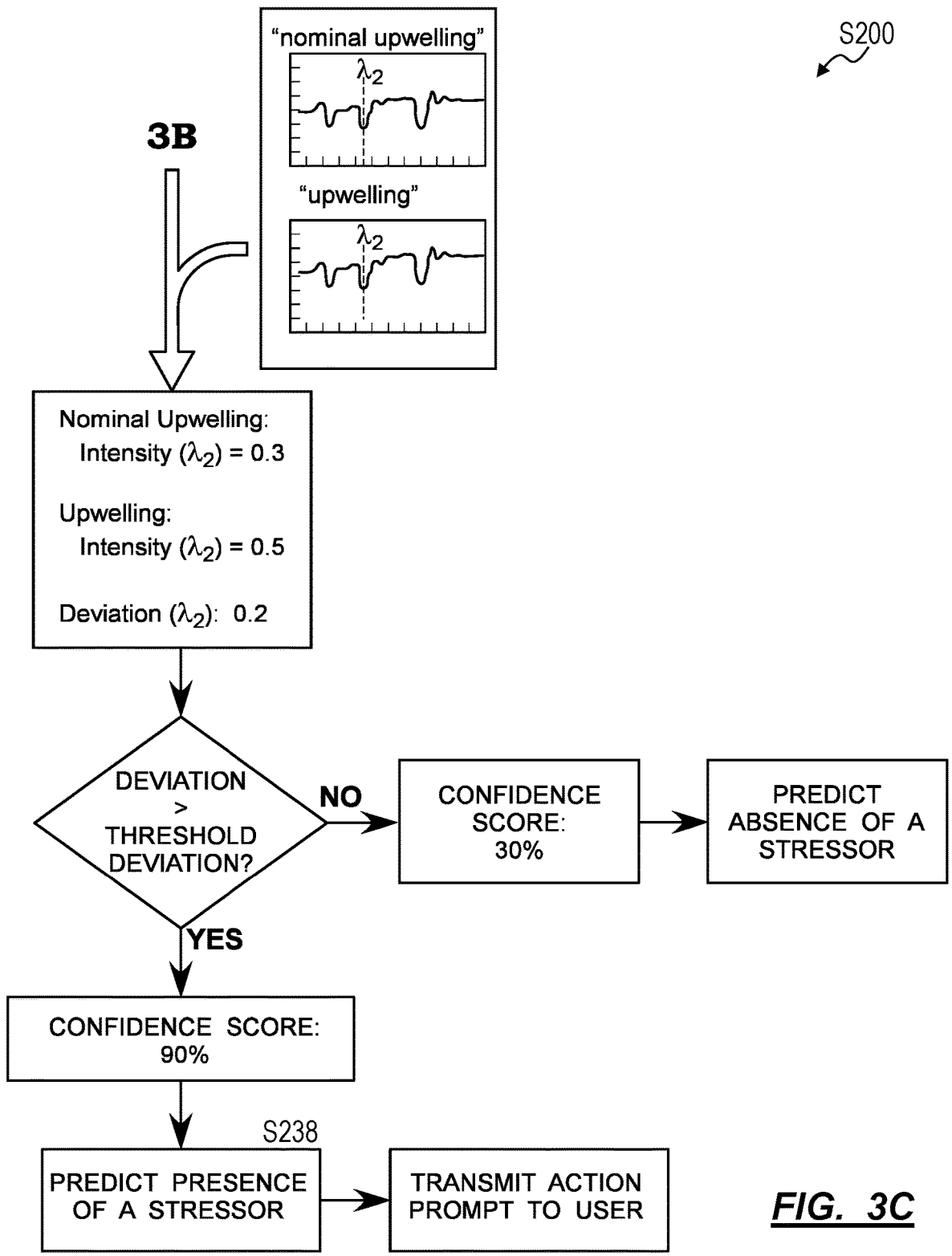

The computer system can extract characteristics from the set of hyperspectral images to predict presence of stressors at the sensor plant. For example, the computer system can access a first hyperspectral image depicting a downwelling light spectrum and a second hyperspectral image depicting an upwelling light spectrum. Then, the computer system can: estimate a nominal upwelling light spectrum based on the downwelling light spectrum represented in the first hyperspectral image, the nominal upwelling light spectrum representing reflectance and fluorescence of the sensor plant, absent the first stressor, in the presence of light according to the downwelling light spectrum at the first time; extract a first intensity, at a first wavelength, in the upwelling light spectrum represented in the second hyperspectral image; extract a first nominal intensity, at the first wavelength, in the nominal upwelling light spectrum; calculate a first deviation between the first intensity and the first nominal intensity at the first wavelength; and, in response to the first deviation exceeding a threshold deviation, predict presence of the first stressor at the sensor plant. Additionally, as shown in FIG. 3C, the computer system can: extract a second intensity, at a second wavelength, in the upwelling light spectrum represented in the second hyperspectral image; extract a second nominal intensity at the second wavelength, in the nominal upwelling light spectrum; calculate a second deviation between the second intensity and the second nominal intensity at the second wavelength; and, in response to the second deviation exceeding the threshold deviation, predict presence of the first stressor at the sensor plant. Therefore, the computer system can predict presence of a stressor at a sensor plant based on the upwelling light spectrum, the downwelling light spectrum, and the nominal upwelling light spectrum (e.g., as defined by the upwelling light model).

In one variation, as shown in FIGS. 3B and 3C, the computer system can calculate a confidence score for a particular stressor representative of the user's confidence that the particular stressor is present at the sensor plant. For example, the computer system can: calculate a first deviation between a first intensity at a first wavelength in an upwelling light spectrum and a first nominal intensity at the first wavelength in a nominal upwelling light spectrum; and calculate a first confidence score based on the first deviation. Then, in response to predicting presence of a first stressor based on the first deviation, the computer system can: calculate a second deviation between a second intensity at a second wavelength in the upwelling light spectrum and a second nominal intensity at the second wavelength in the nominal upwelling light spectrum; calculate a second confidence score based on the first deviation and the second deviation, the second confidence score greater than the first confidence score; and, in response to the second confidence score exceeding a threshold confidence score, predict presence of the first stressor. Alternatively, in response to the second deviation falling below the threshold deviation, the computer system can: calculate a third confidence score based on the first deviation and the second deviation, the third confidence score less than the first confidence score; and, in response to the third confidence score falling below a threshold confidence score, predict absence of the first stressor at the sensor plant.

In one example, the computer system can calculate a first deviation of 10% between a first intensity at a first wavelength in an upwelling light spectrum and a first nominal intensity at the first wavelength in a nominal upwelling light spectrum. Then, in response to the deviation exceeding a threshold deviation, the computer system can: calculate a first confidence score of 50% based on the first deviation; calculate a second deviation of 10% between a second intensity at a second wavelength in the measured upwelling light spectrum and a second nominal intensity at the second wavelength in the nominal upwelling light spectrum; calculate a second confidence score of 90% based on the first deviation and the second deviation; and, in response to the confidence score exceeding a threshold confidence score, predict presence of the first stressor at the sensor plant.

In one variation, in response to predicting presence of a stressor, the computer system can isolate an action that may mitigate the stressor, and suggest this action to a user associated with the crop including the sensor plant. For example, in response to identifying a first stressor present at the sensor plant, the computer system can: isolate a first action, in a set of actions defined for the sensor plant type, linked to the first stressor; and transmitting a notification to perform the first action at the crop to mitigate the first stressor to a computing device of a user associated with the crop. Therefore, the computer system can alert the user of stressors present in the crop and suggest particular actions for mitigating these stressors.

2.4.1 Stressor Magnitude

In one variation, the computer system can identify a magnitude of a particular stressor based on intensity of the upwelling light spectrum at a particular wavelength. In this variation, the computer system can identify a particular wavelength (or range of wavelengths) at which a particular promoter-reporter pair produces a detectable signal. The computer system can then measure intensity of upwelling light at these frequencies to determine presence of a stressor at the sensor plant and to determine a stressor magnitude (e.g., an extent to which it is present). For example, the user may genetically modify a sensor plant to include a first promoter-reporter pair configured to signal presence of a first stressor and to generate maximum red fluorescence at approximately 580 nanometers in the presence of the first stressor. Upon predicting presence of the first stressor at the sensor plant, based on a set of hyperspectral images depicting a downwelling light spectrum and an upwelling light spectrum, the computer system can measure an intensity of the upwelling light spectrum at 580 nm. In response to measuring a relatively high intensity, the computer system can predict a relatively high magnitude of the first stressor at the sensor plant. Alternatively, in response to measuring a relatively low intensity, the computer system can predict a relatively low magnitude of the first stressor at the sensor plant. Therefore, the computer system can estimate the magnitude of a particular stressor at the sensor plant based on the strength (e.g., intensity) of the signal produced by the sensor plant.

In one implementation, the computer system can determine stressor magnitude based on intensity changes within a narrow range of wavelengths in upwelling light. For example, the computer system can, at a first time: extract a first intensity, at a first wavelength, and a second intensity, at a second wavelength in an upwelling light spectrum represented in a hyperspectral image of a sensor plant; and extract a first nominal intensity, at the first wavelength, and a second nominal intensity, at the second wavelength, in a nominal upwelling light spectrum. Then, the computer system can: extract a first area in the upwelling light spectrum between the first wavelength and the second wavelength, based on the first intensity and the second intensity; extract a nominal area in the nominal upwelling light spectrum between the first wavelength and the second wavelength, based on the first nominal intensity and the second nominal intensity; calculate a difference between the first area and the nominal area; and estimate a magnitude of the first stressor present at the sensor plant proportional to the difference. The computer system can select the first wavelength and the second wavelength based on wavelengths at which the particular reporter of the sensor plant is expected to generate fluorescence. Therefore, the computer system can estimate the magnitude of a particular stressor present at the sensor plant based on the strength (e.g., intensity) of the signal produced by the sensor plant over a narrow range of wavelengths corresponding to fluorescence of a particular reporter associated with the particular stressor.

2.4.2 Detection of Promoter-Reporter Pair Signals

In one variation, the computer system can detect solar-induced fluorescent signals by implementing narrow-wavelength measurements near dark spectral features in incident solar radiation. Narrow band techniques associated with Fraunhofer lines (from absorption in the solar atmosphere) and Telluric lines (which originate from absorption of molecules in Earth's atmosphere) enable measurement of the optical signals in daylight, without implementing external illumination. The computer system can extract narrow-wavelength measurements (e.g., at these Fraunhofer lines and/or Telluric lines) from hyperspectral images of the sensor plant to identify fluorescent signals produced by the sensor plant. By extracting these narrow-wavelength measurements, the computer system can detect small, obscure signals with both specificity and accuracy, and detect these signals from hyperspectral images collected both on the ground and airborne. Therefore, the computer system can detect signals produced by sensor plants in hyperspectral images collected from a large range of distances.

The computer system can access hyperspectral images of the sensor plant collected from close ranges. For example, the computer system can access hyperspectral images of a sensor plant collected from tools mounted on top of self-propelled equipment, such as a pole placed in a crop mounted with a device for collecting images of the sensing plants, as shown in FIG. 6. In another example, the computer system can access hyperspectral images of the sensor plant captured manually by a farmer operating a drone (or "UAV") or dispatching an autonomous drone to scan regions of a crop where sensing plants are located to collect images of these sensing plants. In one implementation, the computer system can access hyperspectral images of the sensor plant captured by a sensing device configured to install (e.g., clamp) onto a leaf or stalk of the sensing plant and to capture close-range images of fluorescing surfaces on the sensing plant at a high frequency (e.g., once per minute, once per hour). In these examples, the computer system can access these hyperspectral images from a remote database, the hyperspectral images uploaded to the remote database via a cellular network or downloaded to a mobile device or vehicle via a local ad hoc wireless network when a mobile device or vehicle is nearby, and then uploaded from the mobile device or vehicle to the remote database. In another implementation, the computer system can access hyperspectral images manually collected by a farmer on a mobile device. In this implementation, the computer system can access the hyperspectral images collected on the mobile device, the hyperspectral images electronically uploaded to remote storage or automatically uploaded via a native or web-based agricultural application executing on the mobile device. The computer system can interpret pressures on this plant directly from features extracted from these close-range images to generate a high-resolution, short-interval time-series representation of the health of this sensing plant. The computer system can then combine this high-resolution, short-interval timeseries representation of the health of this sensing plant with features extracted from low-frequency, wider field-of-view images of clusters of plants or a whole field containing this sensing plant to predict the health of multiple or all plants in this field.

Alternatively, the computer system can access hyperspectral images of sensor plants collected from mid-range distances to collect wavelength measurements, the hyperspectral images captured from manned or unmanned vehicles. In one implementation, the computer system can access hyperspectral images of a sensor plant captured by a farmer driving a vehicle along an edge of a crop or a specific region of the crop that contains sensing plants, and collecting images via a handheld device or a device mounted on the farmer's vehicle. The computer system can then access these hyperspectral images from the remote database, time-stamped, and georeferenced, upon upload or at a later time.

In another variation, the computer system can access hyperspectral images captured from long range distances to collect wavelength measurements. The computer system can access hyperspectral images of the agricultural fields captured by long-duration, high-altitude manned or unmanned aerial vehicles, or by satellites such as OCO-2 or GOSAT. For example, the computer system can access satellite images of entire agricultural fields, including multiple clusters of sensing plants. These hyperspectral images can be accessed with a lower frequency and at a lower resolution than images accessed from a close-range optical sensor such as a mobile device. Therefore, the computer system can access hyperspectral images collected from both long-range distances and short-range distances.

The computer system can access hyperspectral images captured by these various methods of collecting hyperspectral images of sensor plants from a range of distances and at various image resolution and extract wavelength measurements to collect high-quality data that enable rapid, targeted responses to certain plant stressors and therefore increase yield of plants nearby in the same agricultural field. In one implementation, the computer system can access hyperspectral images captured at a pole mounted with a high-resolution optical sensor (e.g., a RGB camera, a multispectral camera or spectrometer, a thermal or IR camera) and located in the center of a first cluster of sensing plants in a crop, the optical sensor configured to capture high-resolution images of the sensing plants at multiple times each day and upload the hyperspectral images to a remote database. The computer system can access these high-resolution images from the remote database to collect stressor data for the specific cluster of sensing plants. Additionally, the computer system can access hyperspectral images collected by a satellite configured to capture low-resolution images of the entire crop, which may include multiple sensing plant clusters, such as once per two-week interval. The computer system can then: access these hyperspectral images from a satellite image database; generate a model to link behaviors of the first sensing plant cluster to the other clusters in the crop based on the daily behavior of the first cluster and the biweekly behavior of all sensing plant clusters in the crop; and interpolate behavior of the crop as a whole in regions with or without sensing plants. In another example, when the computer system calculates a certain pressure at the first sensing plant cluster, it also signals the farmer or agronomist to collect a leaf or soil sample from a region of the crop containing the sensing plant cluster, and to test the sample for an exact pressure reading. The computer system can then access this measurement to link data and stressors detected by the sensing plants to the pressure magnitude in the plants.

The computer system can access hyperspectral images of sensor plants collected from a variety of devices, such as from a handheld camera, a handheld spectrometer, a mobile phone, or from any other device that includes a high-resolution spectrometer, includes band-specific coatings, or is otherwise configured to detect wavelengths of electro-magnetic radiation fluoresced, luminescence, or passed by the sensing plant in the presence of a particular stressor. In one variation, the computer system can access hyperspectral images collected from a variety of instrumentation, as different instrumentation can be used depending on the compound of interest, as the wavelengths of different compounds are each best observed under different conditions and may require distinct modes of detection.

3. Third Method

Figure 4A:
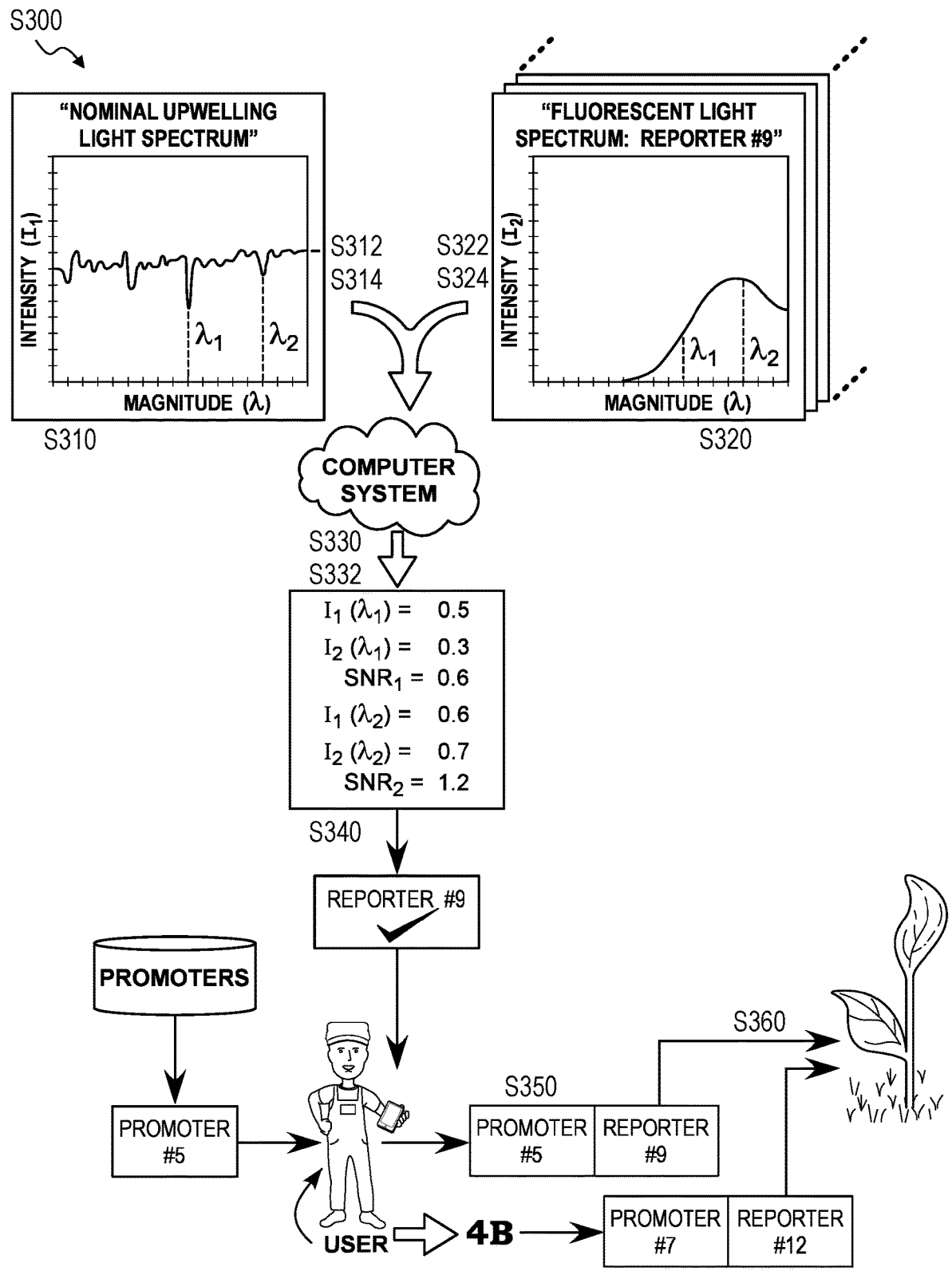
FIGS. 4A and 4B are a flowchart representation of a third method.

As shown in FIG. 4A, a third method S300 for method for selecting reporters for detection of stressors in crops based on fluorescence of sensor plants includes: accessing a nominal upwelling light spectrum representative of reflectance and fluorescence within an area of a crop in Block S310; extracting a nominal peak intensity, at a first wavelength, in the nominal upwelling light spectrum for the area of the crop in Block S312; accessing a first fluorescent light spectrum depicting fluorescence of a first reporter gene, in a set of reporters, when expressed in Block S320; extracting a first peak intensity, at the first wavelength, in the first fluorescent light spectrum of the first reporter gene in Block S322; calculating a first signal-to-noise ratio of the first peak intensity of the first reporter to the nominal intensity for the area of the crop in Block S330; and, in response to the first signal-to-noise ratio exceeding a threshold signal-to-noise ratio, selecting the first reporter gene in Block S340. The third method S300 further includes: pairing a first promoter gene, from a set of promoter genes, linked to a first stressor, in a set of stressors, with the first reporter gene to form a first promoter-reporter pair configured to trigger fluorescence in the presence of the first stressor in Block S350; and genetically modifying a sensor plant to include the first promoter-reporter pair to configure the sensor plant to signal presence of the first stressor in Block S360.

3.1 Applications

Generally, a system—such as a local or remote computer system in conjunction with a user (e.g., a laboratory technician, an operator)—can execute Blocks of the third method S300 to design a sensor plant to include a promoter-reporter pair configured to detect a particular stressor present at the sensor plant and produce a detectable signal (e.g., in the electromagnetic spectrum) upon detection of the particular stressor. In particular, a user can genetically modify a sensor plant to include a promoter configured to activate in the presence of (e.g., "linked to") a particular stressor; and a reporter paired to the promoter and configured to exhibit (or "express") a signal when the promoter is active in the sensor plant. For example, the computer system can cooperate with the user to genetically modify a sensor plant to actively produce a signal (e.g., actively fluoresce)—without excitation of the sensor plant—in the presence of a stressor, the signal configured for detection via passive remote detection. Therefore, the computer system can cooperate with the user to genetically modify sensor plants to include promoter-reporter pairs that generate readily detectable signals in the presence of these stressors.

The computer system can select (or guide the user toward selecting) a reporter for a particular promoter-reporter pair based on particular wavelengths or ranges of wavelengths (e.g., narrow bands) at which the reporter produces a detectable signal in a sensor plant. More specifically, the computer system (or the user, under guidance of the computer system) can select a reporter that generates a measurable difference in an upwelling light spectrum of the sensor plant in the presence of a stressor, when compared to a model upwelling light spectrum representative of the sensor plant in the absence of the stressor. For example, the computer system can select (or suggest to a user) a first reporter that generates fluorescence of the sensor plant between 540 nanometers and 660 nanometers in the electromagnetic spectrum. To increase detectability of signals produced by the sensor plant (e.g., via the reporter), the computer system can select a reporter that generates fluorescence at particular wavelengths at which solar spectra exhibit sharp decreases in wavelength intensity. For example, as shown in FIGS. 7A and 7B, the computer system can select a reporter that generates fluorescence of the sensor plant about Fraunhofer Lines present in solar spectra. Alternatively, the computer system can select a reporter that generates fluorescence of the sensor plant about Telluric Lines present in solar spectra.

In one implementation, the computer system can select reporters based on a signal-to-noise ratio of a fluorescence signal generated by a sensor plant in the presence of stressor to upwelling light captured at the sensor plant absent the stressor. For example, the computer system can: calculate a signal-to-noise ratio (e.g., at a particular wavelength, over a range of wavelengths) of fluorescence generated by the sensor plant in the presence of the stressor, the sensor plant including a particular promoter-reporter pair, to upwelling light captured at the sensor plant in the absence of the stressor; and, in response to the signal-to-noise ratio exceeding a threshold signal-to-noise ratio, select the particular reporter for inclusion in a first promoter-reporter pair. Thus, by selecting reporters that generate a relatively high signal-to-noise ratio, the computer system can enable detection of the signal generated by the sensor plant in the presence of a stressor.

Upon selection of a first reporter, the computer system can pair the first reporter with a first promoter (or suggest pairing the first reporter with a first promoter to a user) to form a first promoter-reporter pair configured to detect and signal presence of a first stressor. The computer system can select (or suggest) the first promoter based on a type of stressor linked with the first promoter. Once paired with the promoter, the computer system can genetically modify a sensor plant to include the first promoter-reporter pair, the sensor plant configured to signal presence of the first stressor at the sensor plant. Additionally, the computer system can genetically modify the sensor plant to include multiple promoter-reporter pairs.

3.2 Promoter-Reporter Pair

A user can genetically modify a sensor plant to include a promoter-reporter pair configured to signal presence of a stressor at the sensor plant. The computer system can: select a promoter linked to a particular stressor for a promoter-reporter pair; select a reporter corresponding to a particular solar induced fluorescence spectrum (hereinafter "fluorescence spectrum"); and pair the promoter and the reporter (e.g. suggest pairing the promoter and the reporter to a user) to form a promoter-reporter pair. Thus, the computer system can select a promoter-reporter pair (e.g. suggest a promoter-reporter pair to a user) for genetically modifying a sensor plant to include the promoter-reporter pair, the sensor plant configured to fluoresce in the presence of the particular stressor.

The sensor plant can include a promoter-reporter pair configured to signal presence of particular biotic and/or abiotic pressures experienced by the sensor plant, such as pest, disease, water, heat, soil health, and/or nutrient stresses or deficiencies. For example, the sensor plant can be genetically modified to include a promoter with activity linked to presence of one stressor at the plant, such as a fungal, pest, heat, water, disease, or nutrient stress. The sensor plant can also be genetically modified to include a reporter paired with the promoter and configured to produce a detectable signal—such as an electromagnetic signal in the visible light or infrared spectrum—when the corresponding promoter is activated. For example, the reporter in the sensor plant can be configured to fluoresce (i.e., produce a signal in the visible spectrum) when the corresponding promoter is active in the sensor plant. More specifically, a promoter-reporter pair can be incorporated into the sensor plant via molecular binding and metabolic engineering techniques that associate expression of a promoter responsive to a particular biological stress with a reporter that produces a measurable signal when the promoter expresses. The promoter-reporter pair can be configured to produce a measurable signal by pairing the reporter with the promoter such that when the promoter expresses the reporter also expresses. Therefore, via expression of the reporter, the promoter-reporter pair can produce a measurable signal of a particular biological stress or trait in the sensor plant.

The computer system can pair promoters and reporters to form a set of promoter-reporter pairs. The computer system can select promoter-reporter pairs based on detectability of signals generated by reporters and suggest these promoter-reporter pairs to a user for inclusion in genetically modified sensor plants. To select reporters, the computer system can compare fluorescence generated by reporters to nominal upwelling light. In one example, the computer system can: access a nominal upwelling light spectrum representative of reflectance and fluorescence within an area of a crop; extract a nominal peak intensity, at a first wavelength, in the nominal upwelling light spectrum for the area of the crop; access a fluorescent light spectrum corresponding to a red-fluorescence protein; extract a first fluorescent light spectrum depicting fluorescence of the red-fluorescence protein, when expressed; and, in response to a first signal-to-noise ratio between the first peak intensity and the first nominal intensity exceeding a threshold signal-to-noise ratio, select the first reporter gene. Then, the computer system can: pair a first promoter linked to plant dehydration to the red-fluorescence protein to form the first promoter-reporter pair; and genetically modify the sensor plant to include the first promoter-reporter pair, the sensor plant configured to fluoresce at the first intensity at the first wavelength in response to dehydration of the sensor plant.

3.2 Nominal Upwelling Light

The computer system can access a nominal upwelling light spectrum to enable selection of reporters for promoter-reporter pairs, the nominal upwelling light spectrum representative of upwelling light at a sensor plant or within an area surrounding a sensor plant, absent stressors. In one variation, the computer system can access the nominal upwelling light spectrum to find regions of the electromagnetic spectrum at which a reporter generated fluorescence signal in the presence of a stressor may exhibit a high signal-to-noise ratio compared to nominal upwelling light in the absence of the stressor.

The computer system can generate a nominal upwelling light spectrum that accounts for reflected light (e.g., as a function of downwelling light), plant fluorescence (e.g., in the absence of a stressor), and fluorescence of other environmental factors (e.g., other plants, soil). Therefore, the computer system can generate a set of nominal upwelling light spectra, each corresponding to a unique environment (e.g., geographic region, area within a crop, etc.)

The computer system can access the nominal upwelling light spectrum when selecting reporters for detection of stressors at the sensor plant. For example, the computer system can: access a nominal upwelling light spectrum representative of reflectance and fluorescence within an area of a crop; extract a nominal peak intensity, at a first wavelength, in the nominal upwelling light spectrum for the area of the crop; access a first fluorescent light spectrum depicting fluorescence of a first reporter gene, in a set of reporters, when expressed; extract a first peak intensity, at the first wavelength, in the first fluorescent light spectrum of the first reporter gene; calculate a signal-to-noise ratio of the first peak intensity of the first reporter to the nominal intensity for the area of the crop; and, in response to the first signal-to-noise ratio exceeding a threshold signal-to-noise ratio, select the first reporter gene. Therefore, the computer system can access the nominal upwelling light spectrum to check detectability of a particular reporter.

3.4 Fluorescent Light Spectrum

The computer system can access fluorescent light spectra corresponding to particular reporters in order to select reporters for promoter-reporter pairs. For example, the computer system can access: a first fluorescent light spectrum depicting fluorescence of a first reporter gene, in a set of reporters, when expressed; a second fluorescent light spectrum depicting fluorescence of a second reporter gene, in the set of reporters, when expressed; and a third fluorescent light spectrum depicting fluorescence of a third reporter gene, in a set of reporters, when expressed. The computer system can extract characteristics of these fluorescent light spectra to determine whether a particular reporter is detectable.

The computer system can compare detectable characteristics of a fluorescent light spectrum of a particular reporter to detectable characteristics of a nominal upwelling light spectrum to determine detectability of a particular reporter. For example, the computer system can: access a first fluorescent light spectrum depicting fluorescence of a first reporter gene, in a set of reporters, when expressed; and extract a first peak intensity, at a first wavelength, in the first fluorescent light spectrum of the first reporter gene. The computer system can then select the first reporter based on the first peak intensity at the first wavelength. Additionally, the computer system can select a particular wavelength or bands of wavelengths (e.g. range of wavelengths) at which to extract the peak intensity of the fluorescent light spectrum. For example, the computer system can extract a first peak intensity, at a first wavelength corresponding to a Telluric line in a nominal upwelling light spectrum, in the first fluorescent light spectrum of the first reporter gene. Therefore, the computer system can select reporters for promoter-reporter pairs based on detectability of a signal generated by the reporter in comparison to nominal upwelling light.

3.5.1 Signal-to-Noise Ratio

A user (e.g., technician, scientist, laboratory, etc.) may select a reporter based on wavelengths at which the sensor plant will fluoresce in the presence of a particular pressure. More specifically, the user may select a reporter that fluoresces at a particular wavelength (or a particular range of wavelengths) and at a particular intensity in the presence of a stressor, such that fluorescence generated by the sensor plant including the reporter is distinguishable from fluorescence generated by other environmental factors (e.g., other plants, soil, rocks).

In one implementation, the user may compare intensities between peaks of the same wavelength in a fluorescent light spectrum of a reporter and in a nominal upwelling light spectrum representative of upwelling light at the sensor plant absent a stressor. In this implementation, the user may select the reporter for a sensor plant based on a high signal-to-noise ratio between the intensity of a first peak in the fluorescent light spectrum of the reporter and the intensity of a nominal peak in the nominal upwelling light spectrum, the first peak and the nominal peak at the same wavelength. For example, the computer system can: access a nominal upwelling light spectrum representative of reflectance and fluorescence within an area of a crop; extract a nominal peak intensity, at a first wavelength, in the nominal upwelling light spectrum for the area of the crop; access a first fluorescent light spectrum depicting fluorescence of a first reporter gene, in a set of reporters, when expressed; extract a first peak intensity, at the first wavelength, in the first fluorescent light spectrum of the first reporter gene; calculate a first signal-to-noise ratio of the first peak intensity of the first reporter to the nominal intensity for the area of the crop; and, in response to the first signal-to-noise ratio exceeding a threshold signal-to-noise ratio, select the first reporter gene. The computer system can then pair (e.g. suggest pairing to the user) the first reporter with a first promoter linked to a first stressor (e.g., plant dehydration) to form a first promoter-reporter pair configured to signal presence of the first stressor and enable a user to genetically modify a sensor plant to include the first promoter-reporter pair. Thus, by selecting the first promoter-reporter pair, the computer system can enable a user to genetically modify the sensor plant to signal presence of the first stressor.

Additionally, in one variation, as shown in FIG. 4A, the computer system can check the signal-to-noise ratio within a narrow band of wavelengths, by calculating the signal-to-noise ratio at additional wavelengths (e.g., at a second wavelength). For example, in response to the first signal-to-noise ratio exceeding a threshold signal-to-noise ratio, the computer system can: extract a second nominal peak intensity in Block S314, at a second wavelength, in the nominal upwelling light spectrum for the area of the crop; extract a second peak intensity in Block S324, at the second wavelength, in the first fluorescent light spectrum of the first reporter gene; calculate a second signal-to-noise ratio of the second intensity of the first reporter gene to the nominal intensity for the area of the crop in Block S332; and, in response to the second signal-to-noise ratio exceeding the threshold signal-to-noise ratio, select the first reporter gene. Therefore, the computer system can check that the reporter generates a signal that is detectable across a range of wavelengths.

3.7 Multiple Promoter-Reporter Pairs

In one implementation, the computer system can select multiple promoter-reporter pairs for inclusion in a particular sensor plant. For example, the computer system can initially select a first reporter, in a set of reporters, for inclusion in a sensor plant based on a first signal-to-noise ratio between upwelling light in the presence of a first stressor (e.g., including fluorescence generated by the reporter) and upwelling light in the absence of the first stressor, the first reporter paired with a first promoter to form a first promoter-reporter pair configured to signal presence of the first stressor. Then, the computer system can: select a second reporter; combine the second promoter linked to a second stressor with the second reporter to form a second promoter-reporter pair configured to signal presence of the second stressor; and genetically modify the first promoter-reporter pair and the second promoter-reporter pair, the sensor plant configured to signal presence of the first stressor and the second stressor at the sensor plant.

Figure 4B:
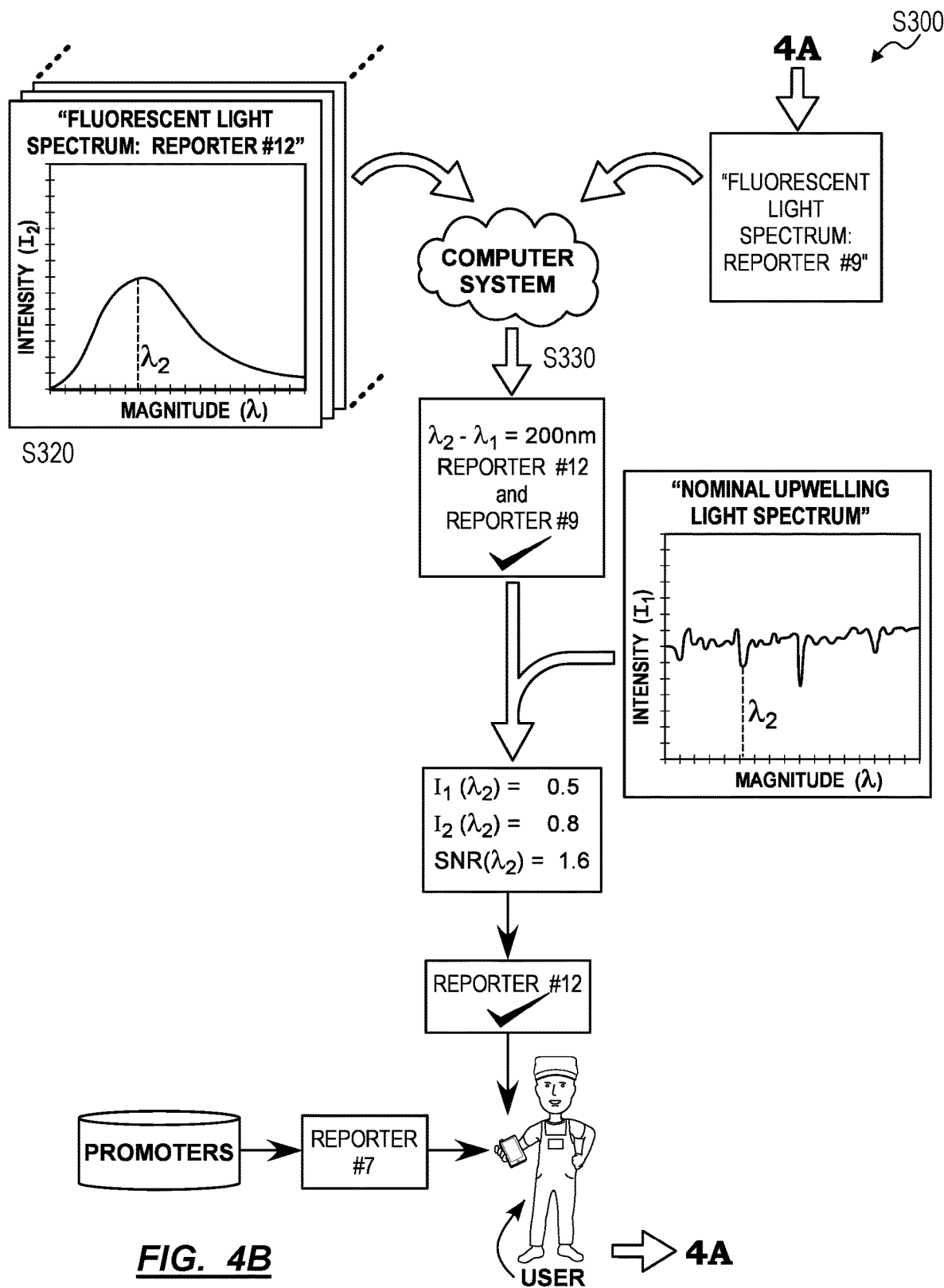

The computer system can select multiple reporters based on a calculated signal-to-noise ratio with the model upwelling light spectrum as described above, and/or based on minimizing overlapping signals between reporters. For example, as shown in FIG. 4B, in response to selecting a first reporter exhibiting a maximum signal-to-noise ratio at a first wavelength, the computer system can access a fluorescent light spectrum corresponding to a second reporter. Then, in response to the fluorescent light spectrum exhibiting a peak at a second wavelength, the second wavelength a minimum distance from the first wavelength, the computer system can: calculate a signal-to-noise ratio of an intensity of the peak in the fluorescent light spectrum at a second wavelength to a nominal intensity of a nominal upwelling light spectrum at the second wavelength (e.g., in the absence of any stressor); and, in response to the second signal-to-noise ratio exceeding the threshold signal-to-noise ratio, select the second reporter.

In one example, the computer system can genetically modify the sensor plant to include: a first promoter-reporter pair configured to fluoresce at a first wavelength at a first intensity in response to presence of a first stressor; and a second promoter-reporter pair configured to fluoresce at a second wavelength at a second intensity in response to presence of a second stressor.

The computer system can pair each selected reporter with a particular promoter to form promoter-reporter pairs configured to detect and signal the presence of a set of stressors. In one variation, the computer system can: select a first promoter linked to a first stressor for pairing with a first reporter to form a first promoter-reporter pair; select a second promoter linked to a second stressor for pairing with a second reporter to form a second promoter-reporter pair; and genetically modify a sensor plant to include the first promoter-reporter pair and the second promoter-reporter pair, the sensor plant configured to signal presence of the first stressor and the second stressor at the sensor plant. For example, the computer system can: select a first promoter linked to a disease pressure and pair the first promoter with the first reporter to form a first promoter-reporter pair; select a second promoter linked to a bacterial pressure and pair the second promoter with a second reporter to form a second promoter-reporter pair; and genetically modify the sensor plant to include the first promoter-reporter pair and the second promoter-reporter pair, the sensor plant configured to signal presence of the disease pressure and the bacterial pressure at the sensor plant.

The computer systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for identifying stressors in crops based on fluorescence of sensor plants comprising:
   accessing a set of spectral images of a sensor plant sown in a crop, the sensor plant of a sensor plant type including a set of promoters and a set of reporters configured to signal a set of stressors present at the sensor plant, the set of promoters and set of reporters forming a set of promoter-reporter pairs, the set of spectral images comprising:
      a first spectral image depicting a downwelling light spectrum corresponding to solar radiation and captured, at a first time, by an optical spectrometer defining a field of view facing opposite the sensor plant; and
      a second spectral image depicting an upwelling light spectrum captured, at approximately the first time, by the optical spectrometer defining the field of view facing the sensor plant, the upwelling light spectrum comprising a summation of a reflected light spectrum and a fluorescent light spectrum;
   extracting a reporter fluorescent light spectrum from the upwelling light spectrum based on the upwelling light spectrum and the downwelling light spectrum, comprising:
      estimating the reflected light spectrum based on a reflectance factor of the sensor plant, in the presence of light according to the downwelling light spectrum at the first time;
      estimating the fluorescent light spectrum based on a first difference between the upwelling light spectrum and the reflected light spectrum; and
      estimating the reporter fluorescent light spectrum as the fluorescent light spectrum;
   accessing a reporter model linking solar induced fluorescence measurements extracted from downwelling light spectra comprising the downwelling light spectrum and upwelling light spectra comprising the upwelling light spectrum to the set of stressors in plants of the sensor plant type based on signals generated by the set of promoter-reporter pairs in the sensor plant type; and
   identifying a first stressor, in the set of stressors, present at the sensor plant based on the reporter model and solar induced fluorescence measurements extracted from the set of spectral images.

2. The method of claim 1, wherein identifying the first stressor comprises:
   extracting a downwelling intensity, at a wavelength associated with a Fraunhofer line, in the downwelling light spectrum;
   extracting an upwelling intensity, at the wavelength associated with the Fraunhofer line, in the upwelling light spectrum;
   calculating a difference between the upwelling intensity and the downwelling intensity; and
   in response to the difference exceeding a threshold difference, identifying the first stressor present at the sensor plant.

3. The method of claim 1:
   further comprising estimating a nominal upwelling light spectrum based on the downwelling light spectrum represented in the first spectral image, the nominal upwelling light spectrum representing reflectance and fluorescence of the sensor plant, absent the first stressor, in the presence of light according to the downwelling light spectrum at the first time;
   wherein identifying the first stressor comprises:
      extracting a first intensity, at a first wavelength, in the upwelling light spectrum represented in the second spectral image;
      extracting a first nominal intensity, at the first wavelength, in the nominal upwelling light spectrum;
      calculating a first deviation between the first intensity and the first nominal intensity at the first wavelength; and
      in response to the first deviation exceeding a threshold deviation, predicting presence of the first stressor at the sensor plant.

4. The method of claim 3, wherein predicting presence of the first stressor at the sensor plant further comprises, in response to the first deviation exceeding the threshold deviation:
   extracting a second intensity, at a second wavelength, in the upwelling light spectrum represented in the second spectral image;
   extracting a second nominal intensity at the second wavelength, in the nominal upwelling light spectrum;
   calculating a second deviation between the second intensity and the second nominal intensity at the second wavelength; and
   in response to the second deviation exceeding the threshold deviation, predicting presence of the first stressor at the sensor plant.

5. The method of claim 4, further comprising:
   extracting a first area below a curve of the upwelling light spectrum between the first wavelength and the second wavelength, based on the first intensity and the second intensity;
   extracting a nominal area below a curve of the nominal upwelling light spectrum between the first wavelength and the second wavelength, based on the first nominal intensity and the second nominal intensity;
   calculating a difference between the first area and the nominal area; and
   estimating a magnitude of the first stressor present at the sensor plant according to the difference.

6. The method of claim 4:
   wherein predicting presence of the first stressor at the sensor plant in response to the first deviation exceeding a threshold deviation further comprises calculating a first confidence score based on the first deviation; and
   wherein predicting presence of the first stressor at the sensor plant in response to the second deviation exceeding a threshold deviation further comprises calculating a second confidence score based on the first deviation and the second deviation, the second confidence score greater than the first confidence score.

7. The method of claim 6, further comprising:
   in response to the second deviation falling below the threshold deviation, calculating a third confidence score based on the first deviation and the second deviation, the third confidence score less than the first confidence score; and
   in response to the third confidence score falling below a threshold confidence score, predicting absence of the first stressor at the sensor plant.

8. The method of claim 1:
   wherein estimating the reporter fluorescent light spectrum further comprises:
      accessing a nominal fluorescent light spectrum representative of fluorescence within the area of the sensor plant absent the first stressor, in the presence of light according to the downwelling light spectrum at the first time;

calculating a second difference between the fluorescent light spectrum and the nominal fluorescent light spectrum; and estimating the reporter fluorescent light spectrum for the sensor plant based on the second difference.

9. The method of claim 1:

wherein accessing the set of spectral images of the sensor plant comprises accessing the set of spectral images of the sensor plant genetically modified to include:
  a first promoter-reporter pair, in the set of promoter-reporter pairs, configured to fluoresce, at a first intensity, at a first wavelength, in response to presence of the first stressor at the sensor plant; and
  a second promoter-reporter pair, in the set of promoter-reporter pairs, configured to fluoresce, at a second intensity, at a second wavelength, in response to presence of the second stressor at the sensor plant; and wherein identifying the first stressor present at the sensor plant comprises identifying the first stressor based on fluorescence of the sensor plant, at the first intensity, at the first wavelength.

10. The method of claim 1, wherein accessing the set of spectral images of the sensor plant comprises:
  accessing the first spectral image of the sensor plant captured by a spectral sensor mounted to a boom in the crop;
  accessing the second spectral image of the sensor plant captured by a spectral sensor installed on an aerial vehicle; and
  accessing a third spectral image of the sensor plant captured by a spectral sensor installed on a satellite.

11. The method of claim 1, further comprising, in response to identifying the first stressor:
  isolating a first action, in a set of actions defined for the sensor plant type, linked to the first stressor; and
  transmitting a notification to perform the first action at the crop to mitigate the first stressor to a computing device of a user associated with the crop.

12. A method for identifying stressors in crops based on fluorescence of sensor plants comprising:
  accessing a set of spectral images of a sensor plant sown in a crop, the sensor plant of a sensor plant type including a set of promoters and a set of reporters configured to signal a set of stressors present at the sensor plant, the set of promoters and set of reporters forming a set of promoter-reporter pairs, the set of spectral images comprising:
    a first spectral image depicting a downwelling light spectrum corresponding to solar radiation and captured, at a first time, by an optical spectrometer defining a field of view facing opposite the sensor plant; and
    a second spectral image depicting an upwelling light spectrum captured, at approximately the first time, by the optical spectrometer defining the field of view facing the sensor plant;
  accessing a reporter model linking solar induced fluorescence measurements extracted from downwelling light spectra comprising the downwelling light spectrum and upwelling light spectra comprising the upwelling light spectrum to the set of stressors in plants of the sensor plant type based on signals generated by the set of promoter-reporter pairs in the sensor plant type;
  estimating a nominal upwelling light spectrum based on the downwelling light spectrum represented in the first spectral image, the nominal upwelling light spectrum representing reflectance and fluorescence of the sensor plant, absent the first stressor, in the presence of light according to the downwelling light spectrum at the first time;
  extracting a first intensity, at a first wavelength, in the upwelling light spectrum represented in the second spectral image;
  extracting a first nominal intensity, at the first wavelength, in the nominal upwelling light spectrum;
  calculating a first deviation between the first intensity and the first nominal intensity at the first wavelength; and
  in response to the first deviation exceeding a threshold deviation:
    extracting a second intensity, at a second wavelength, in the upwelling light spectrum represented in the second spectral image;
    extracting a second nominal intensity at the second wavelength, in the nominal upwelling light spectrum;
    calculating a second deviation between the second intensity and the second nominal intensity at the second wavelength; and
    in response to the second deviation exceeding the threshold deviation, predicting presence of a first stressor, in the set of stressors, at the sensor plant based on the reporter model and solar induced fluorescence measurements extracted from the set of spectral images.

13. The method of claim 12, further comprising:
  extracting a first area below a curve of the upwelling light spectrum between the first wavelength and the second wavelength, based on the first intensity and the second intensity;
  extracting a nominal area below a curve of the nominal upwelling light spectrum between the first wavelength and the second wavelength, based on the first nominal intensity and the second nominal intensity;
  calculating a difference between the first area and the nominal area; and
  estimating a magnitude of the first stressor present at the sensor plant according to the difference.

14. The method of claim 12:
wherein predicting presence of the first stressor at the sensor plant in response to the first deviation exceeding a threshold deviation further comprises calculating a first confidence score based on the first deviation;
wherein predicting presence of the first stressor at the sensor plant in response to the second deviation exceeding a threshold deviation further comprises calculating a second confidence score based on the first deviation and the second deviation, the second confidence score greater than the first confidence score.

15. The method of claim 14:
in response to the second deviation falling below the threshold deviation, calculating a third confidence score based on the first deviation and the second deviation, the third confidence score less than the first confidence score; and
in response to the third confidence score falling below a threshold confidence score, predicting absence of the first stressor at the sensor plant.

16. The method of claim 12:
wherein accessing the set of spectral images of the sensor plant comprises accessing the set of spectral images of the sensor plant genetically modified to include:
  a first promoter-reporter pair, in the set of promoter-reporter pairs, configured to fluoresce, at a first intensity, at a first wavelength, in response to presence of the first stressor at the sensor plant; and a second promoter-reporter pair, in the set of promoter-reporter pairs, configured to fluoresce, at a second intensity, at a second wavelength, in response to presence of the second stressor at the sensor plant; and wherein identifying the first stressor present at the sensor plant comprises identifying the first stressor based on fluorescence of the sensor plant, at the first intensity, at the first wavelength.

17. The method of claim 12, wherein accessing the set of spectral images of the sensor plant comprises:

accessing the first spectral image of the sensor plant captured by a spectral sensor mounted to a boom in the crop;

accessing the second spectral image of the sensor plant captured by a spectral sensor installed on an aerial vehicle; and accessing a third spectral image of the sensor plant captured by a spectral sensor installed on a satellite.

18. The method of claim 12, further comprising, in response to predicting presence of the first stressor:

isolating a first action, in a set of actions defined for the sensor plant type, linked to the first stressor; and transmitting a notification to perform the first action at the crop to mitigate the first stressor to a computing device of a user associated with the crop.

* * * * *